(12) United States Patent
Goldstein et al.

(10) Patent No.: US 12,201,708 B2
(45) Date of Patent: *Jan. 21, 2025

(54) MICROCAPSULES COMPRISING SUNSCREEN AGENTS

(71) Applicant: Tagra Biotechnologies Ltd., Natania (IL)

(72) Inventors: Danny Goldstein, Kibbutz Dafna (IL); Olga Privalova, Kibbutz LeHavot HaBashan (IL); Lior Ben-Altabet, Doar-Na Galil Elyon (IL); Yaniv Menachem, Moshav Dishon (IL); Hanan Haj, Rehaniya (IL)

(73) Assignee: Tagra Biotechnologies Ltd., Natania (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/884,160

(22) Filed: May 27, 2020

(65) Prior Publication Data
US 2020/0281827 A1    Sep. 10, 2020

Related U.S. Application Data

(63) Continuation of application No. 14/770,873, filed as application No. PCT/IL2014/050207 on Feb. 27, 2014, now abandoned.

(Continued)

(51) Int. Cl.
*A61K 8/11*    (2006.01)
*A61K 8/29*    (2006.01)
(Continued)

(52) U.S. Cl.
CPC .............. *A61K 8/11* (2013.01); *A61K 8/29* (2013.01); *A61K 8/35* (2013.01); *A61K 8/40* (2013.01);
(Continued)

(58) Field of Classification Search
CPC .............. A61K 8/40; A61K 8/11; A61K 8/35; A61K 8/29; A61K 8/8152; A61K 2800/262;
(Continued)

(56) References Cited

U.S. PATENT DOCUMENTS 3,737,337 A    6/1973   Schnoring et al.
4,588,639 A    5/1986   Ozono
(Continued)

FOREIGN PATENT DOCUMENTS

CN    101309746    11/2008
EP    1899015    3/2008
(Continued)

OTHER PUBLICATIONS

Bemotrizinol, [(retrieved from on-line website: https://pubchem.ncbi.nlm.nih.gov/compound/Bemotrizinol), last visit Feb. 3, 2021]. (Year: 2021).*

(Continued)

*Primary Examiner* — Kyung S Chang

(57) ABSTRACT

Microcapsules comprised of a core comprising one or more sunscreen agents and a shell of a wall-forming polymeric material, which are non-rupturable upon rubbing or pressing on the skin, and processes of preparing same are disclosed. Topical formulations comprising the microcapsules, which can be, for example, sunscreen formulations or skin care formulations, are also provided.

12 Claims, 5 Drawing Sheets

Related U.S. Application Data

(60) Provisional application No. 61/770,773, filed on Feb. 28, 2013.

(51) Int. Cl.
*A61K 8/35* (2006.01)
*A61K 8/40* (2006.01)
*A61K 8/81* (2006.01)
*A61Q 17/04* (2006.01)
*A61Q 19/00* (2006.01)

(52) U.S. Cl.
CPC .............. *A61K 8/8152* (2013.01); *A61Q 17/04* (2013.01); *A61K 2800/262* (2013.01); *A61K 2800/30* (2013.01); *A61K 2800/412* (2013.01); *A61K 2800/52* (2013.01); *A61K 2800/805* (2013.01); *A61Q 19/00* (2013.01)

(58) Field of Classification Search
CPC .......... A61K 2800/30; A61K 2800/805; A61K 2800/412; A61Q 19/00; A61Q 17/04
See application file for complete search history.

(56) References Cited

U.S. PATENT DOCUMENTS

| | | | |
|---|---|---|---|
| 5,455,048 | A | 10/1995 | Lahmani et al. |
| 6,242,099 | B1 | 6/2001 | Grandmontagne et al. |
| 6,303,149 | B1 | 10/2001 | Magdassi et al. |
| 6,932,984 | B1 | 8/2005 | Babtsov et al. |
| 7,838,037 | B2 | 11/2010 | Kvitnitsky et al. |
| 2007/0059258 | A1 | 3/2007 | Chaudhuri |
| 2009/0053153 | A1 | 2/2009 | Lee et al. |
| 2009/0155371 | A1 | 6/2009 | Sojka et al. |
| 2010/0040696 | A1 | 2/2010 | Sente et al. |
| 2012/0148647 | A1 | 6/2012 | Walzel et al. |
| 2016/0008237 | A1 | 1/2016 | Goldstein et al. |

FOREIGN PATENT DOCUMENTS

| | | |
|---|---|---|
| JP | 07-291837 | 11/1995 |
| JP | 09-118726 | 5/1997 |
| JP | 09-194343 | 7/1997 |
| JP | 2001-096146 | 4/2001 |
| WO | WO 2009/138978 | 11/2009 |
| WO | WO 2011/020928 | 2/2011 |
| WO | WO 2012/156965 | 11/2012 |
| WO | WO 2014/132261 | 9/2014 |

OTHER PUBLICATIONS

Iscotrizinol, [(retrieved from on-line website: http://somugroup.com/products/scappl/iscotrizinol.html), last visit Feb. 3, 2021] (Year: 2021).*
Ethylhexyl triazone, [(retrieved from on-line website: https://drugs.ncats.io/substance/XQN8R9SAK4), last visit Feb. 3, 2021] (Year: 2021).*
Diethylaminohydroxybenzoyl hexylbenzoate, [(retrieved from on-line website: https://pubchem.ncbi.nlm.nih.gov/compound/Diethylamino-hydroxybenzoyl-hexyl-benzoate), last visit Feb. 3, 2021 (Year: 2021).*
Oxybenzone, [(retrieved from on-line website: https://pubchem.ncbi.nlm.nih.gov/compound/Oxybenzone), last visit Feb. 3, 2021]. (Year: 2021).*
Dioxybenzone, [(retrieved from on-line website: https://pubchem.ncbi.nlm.nih.gov/compound/dioxybenzone), last visit Feb. 3, 2021] (Year: 2021).*
Kim et al., "Simultaneous analysis and monitoring of 16 UV filters in cosmetics by high-performance liquid chromatography,", Journal of Cosmetic Science, 2012, 63(2):103-117 (abstract is only attached). (Year: 2012).*
Morabito et al., "Review of sunscreen and the emergence of non-conventional absorbers and their applications in ultraviolet protection", Int'l Journal of Cosmetic Science, 2011, 33, pp. 385-390. (Year: 2011).*
Advisory Action Before the Filing of an Appeal Brief Dated Nov. 25, 2019 From the US Patent and Trademark Office Re. U.S. Appl. No. 141770,873. (7 pages).
Applicant-Initiated Interview Summary Dated Jan. 15, 2020 From the US Patent and Trademark Office Re. U.S. Appl. No. 14/770,873. (4 pages).
Communication Pursuant to Article 94(3) EPC Dated May 2, 2017 From the European Patent Office Re. Application No. 14715123.7. (7 Pages).
Communication Pursuant to Article 94(3) EPC Dated Mar. 19, 2019 From the European Patent Office Re. Application No. 14715123.7. (5 Pages).
Communication Pursuant to Article 94(3) EPC Dated Mar. 20, 2018 From the European Patent Office Re. Application No. 14715123.7. (7 Pages).
Communication Relating to the Results of the Partial International Search Dated Jun. 23, 2014 From the International Searching Authority Re. Application No. PC/IL2014/050207.
Decision of Rejection Dated May 10, 2019 From the State Intellectual Property Office of the People's Republic of China Re. Application No. 201480024020.0 and Its Translation Into English. (12 Pages).
Examination Report Dated Nov. 20, 2017 From the Australian Government, IP Australia Re. Application No. 2014222376. (5 Pages).
Examination Report Dated Mar. 31, 2020 From the Sevico Publico Federal, Ministerio da Economia, Instituto Nacional da Propriedade Industrial do Brasil Re. Application No. BR112015020889-4. (4 Pages).
International Preliminary Report on Patentability Dated Sep. 11, 2015 From the International Bureau of WIPO Re. Application No. PC/IL2014/050207.
International Search Report and the Written Opinion Dated Sep. 12, 2014 From the International Searching Authority Re. Application No. PC/IL2014/050207.
Notice of Reason for Rejection Dated Jan. 30, 2018 From the Japan Patent Office Re. Application No. 2015-559603 and Its Summary in English. (8 Pages).
Notification of Office Action and Search Report Dated Apr. 17, 2017 From the State Intellectual Property Office of the People's Republic of China Re. Application No. 201480024020.0. (12 Pages).
Notification of Office Action Dated Jan. 2, 2018 From the State Intellectual Property Office of the People's Republic of China Re. Application No. 201480024020.0 and Its Summary in English. (8 Pages).
Notification of Office Action Dated Jul. 18, 2018 From the State Intellectual Property Office of the People's Republic of China Re. Application No. 201480024020.0 and Its Summary in English. (7 Pages).
Office Action Dated Apr. 25, 2018 From the Israel Patent Office Rc. Application No. 240892 and Its Translation Into English. (8 Pages).
Official Action Dated Oct. 2, 2018 From the US Patent and Trademark Office Re. U.S. Appl. No. 14/770,873. (23 pages).
Official Action Dated Jul. 12, 2019 From the US Patent and Trademark Office Re. U.S. Appl. No. 14/770,873. (20 pages).
Official Action Dated Jan. 17, 2020 From the US Patent and Trademark Office Re. U.S. Appl. No. 14/770,873. (14 pages).
Official Action Dated Apr. 19, 2018 From the US Patent and Trademark Office Re. U.S. Appl. No. 14/770,873. (26 pages).
Official Action Dated Feb. 21, 2019 From the US Patent and Trademark Office Re. U.S. Appl. No. 14/770,873. (11 pages).
Official Action Dated Sep. 21, 2017 From the US Patent and Trademark Office Re. U.S. Appl. No. 14/770,873. (23 pages).
Official Action Dated Jan. 27, 2017 From the US Patent and Trademark Office Rc. U.S. Appl. No. 14/770,873. (21 pages).
Requisition by the Examiner Dated Feb. 11, 2020 From the Innovation, Science and Economic Development Canada, Canadian Intellectual Property Office Re. Application No. 2,902,476.

(56) References Cited

OTHER PUBLICATIONS

Restriction Official Action Dated Oct. 12, 2016 From the US Patent and Trademark Office Re. U.S. Appl. No. 14/770,873.
Search Report and Explanations Dated Jul. 22, 2019 From the National Institute of Industrial Property of Brazil Re. Application No. BR112015020889-4 and Its Summary in English. (5 Pages).
Third Party Submission Dated Mar. 2, 2017 From the Japan Patent Office Re. Application No. 2015-559603 and Its Translation Into English. (22 Pages).
Translation Dated Mar. 6, 2018 of Notice of Reason for Rejection Dated Jan. 30, 2018 From the Japan Patent Office Re. Application No. 2015-559603. (10 Pages).
Translation Dated May 11, 2020 of Examination Report Dated Mar. 31, 2020 From the Sevico Publico Federal, Ministerio da Economia, Instituto Nacional da Propriedade Industrial do Brasil Re. Application No. BR112015020889-4. (4 Pages).
Translation Dated Jun. 26, 2019 of Decision of Rejection Dated May 10, 2019 From the State Intellectual Property Office of the People's Republic of China Rc. Application No. 201480024020.0. (11 Pages).
Translation of Notification of Office Action Dated Jan. 2, 2018 From the State Intellectual Property Office of the People's Republic of China Re. Application No. 201480024020.0. (9 Pages).
Bae et al. "Living Environment and Health in Urban Community", Peking University Press, p. 79-80, Mar. 2008.
Burnett et al. "Current Sunscreen Controversies: A Critical Review", Photodermatology, Photoimmunology & Photomedicine, 27(2): 58-67, Apr. 2011.
Incosmetics "Hybrid UV Filters", Sunjin Newsletter, XP055123245, p. 1-4, 2011. P.1, col. 2, Line 4.
Marcato et al. "Nanostructed Polymer and Lipid Carriers for Sunscreen. Biological Effects and Skin Permeation", Journal of Nanoscience and Nanotechnology, 11(3): 1880-1886, Mar. 2011.
Shaath "SPF Boosters and Photostability of Ultraviolet Filters", Happi, p. 77-83, Oct. 1, 2007.
Sun et al. "Transparent PMMA/ZnO Nanocomposite Films Based on Colloidal ZnO Quantum Dots", Nanotechnology 18(21): pp. 1-7, Apr. 27, 2007.
Sunjin "Hybrid Abomc", Sunjin Newsletter, XP055123242, p. 2-16, Jan. 2, 2011. p. 2-16.
Notice of Re-Examination Dated Jun. 12, 2020 From the State Intellectual Property Office of the People's Republic of China Re. Application No. 201480024020.0 and Its Summary in English. (12 Pages).
Grounds of Reasons of Rejection Dated Jul. 3, 2020 From the Korean Intellectual Property Office Re. Application No. 10-2015-7026771. (7 Pages).
Translation Dated Jul. 22, 2020 of Grounds of Reasons of Rejection Dated Jul. 3, 2020 From the Korean Intellectual Property Office Re. Application No. 10-2015-7026771. (6 Pages).
Communication Pursuant to Article 94(3) EPC Dated Sep. 30, 2020 From the European Patent Office Re. Application No. 20176279.6. (9 Pages).
European Search Report Dated Aug. 6, 2020 From the European Patent Office Re. Application No. 20176279.6. (7 Pages).
Final Official Action Dated Jul. 13, 2020 from the US Patent and Trademark Office Re. U.S. Appl. No. 14/770,873. (20 pages).
Notice of Panel Decision From Pre-Appeal Brief Review Dated Nov. 4, 2020 From the US Patent and Trademark Office Re. U.S. Appl. No. 14/770,873. (2 Pages).
Requisition by the Examiner Dated Sep. 25, 2020 From the Innovation, Science and Economic Development Canada, Canadian Intellectual Property Office Re. Application No. 2,902,476. (4 Pages).
Examiner's Answer Dated Apr. 9, 2021 Before the Patent Trial and Appeal Board of the US Patent and Trademark Office Re. U.S. Appl. No. 14/770,873. (23 Pages).
Grounds of Reasons of Rejection Dated Jan. 27, 2021 From the Korean Intellectual Property Office Re. Application No. 10-2015-7026771 and Its Translation Into English. (13 Pages).
Requisition by the Examiner Dated Mar. 16, 2021 From the Innovation, Science and Economic Development Canada, Canadian Intellectual Property Office Re. Application No. 2,902,476. (3 Pages).
Afonso et al. "Photodegradation of Avobenzone: Stabilization Effect of Antioxidants", Journal of Photochemistry and Photobiology B: Biology, 140: 36-40, Available Online Jul. 15, 2014.
Ground(s) of Reason of Rejection Dated Sep. 28, 2021 From the Korean Intellectual Property Office Re. Application No. 2015-7026771 and Its Translation Into English. (8 Pages).
Requisition by the Examiner Dated Oct. 5, 2021 From the Innovation, Science and Economic Development Canada, Canadian Intellectual Property Office Re. Application No. 2,902,476. (3 Pages).
Communication Pursuant to Article 94(3) EPC Dated Nov. 9, 2022 From the European Patent Office Re. Application No. 20176279.6. (4 Pages).

* cited by examiner

MICROCAPSULES COMPRISING SUNSCREEN AGENTS

RELATED APPLICATIONS

This application continuation of U.S. patent application Ser. No. 14/770,873, filed on Aug. 27, 2015, which is a National Phase of PCT Patent Application No. PCT/IL2014/050207 having International Filing Date of Feb. 27, 2014, which claims the benefit of priority under 35 USC § 119 (e) of U.S. Provisional Patent Application No. 61/770,773 filed on Feb. 28, 2013. The contents of the above applications are all incorporated by reference as if fully set forth herein in their entirety.

FIELD AND BACKGROUND OF THE INVENTION

The present invention, in some embodiments thereof, relates to microcapsules suitable for use in topical compositions and, more particularly, but not exclusively, to microcapsules comprising sunscreen agents and to topical formulations comprising same, which can be used, for example, in cosmetic formulations, such as sunscreen and skincare formulations.

The detrimental effects of UV exposure to the sun have been well described in the literature. Both acute and chronic UV exposures can lead to sunburn, photocarcinogenesis, photo-immunosuppression and photoaging. While the photoprotective benefits of the inorganic UV filters $TiO_2$ and ZnO have been known for decades, these earlier generations of inorganic filters, comprised of large particles, produce an opaque and white appearance on the skin. In addition to cosmetic drawbacks, widespread application of early formulations containing $TiO_2$ or ZnO was further hindered by their poor dispersive properties which resulted in grainy and occlusive qualities. Considerable effort has been made to overcome the cosmetic shortcomings of these inorganic UV filters by progressively minimizing their particle size into the nano range (less than 100 nm).

Nanoparticles are known to exhibit different chemical, mechanical, electrical and optical properties than standard-sized particles. Recently, it was reported, on the basis of in vitro cell experiments, that pure $TiO_2$ or ZnO nanoparticles can induce free radical formation in the presence of light and that this may damage applied therewith. Therefore, the incorporation of $TiO_2$ and ZnO nanoparticles into sunscreens has raised interesting questions regarding the dermal penetration, systemic absorption and subsequent toxicity of these nanoparticles. Currently, there is no in vivo evidence to indicate possible toxicity of nanoparticulate $TiO_2$ or ZnO in humans using sunscreen products. To date, the current weight of evidence indicates that the particles remain on the surface of the skin and in the outer dead layer (stratum corneum) of the skin. Thus, an analysis of the available evidence fails to demonstrate toxicity of these products after cutaneous application to healthy, intact skin. Nevertheless, comprehensive and extensive studies are being sponsored by health authorities in different countries to assess adverse effects of nanoparticles of $TiO_2$ or ZnO on the biological properties of cells and consequent, negative health implications.

Oxybenzone (benzophenone-3) is a widely-used lipophilic broad spectrum molecular sunscreen agent that effectively absorbs ultraviolet B (UVB; 290-320 nm), some ultraviolet A (UVA; 320-360 nm) and some ultraviolet C (250-290 nm) light rays. However, oxybenzone is the most common cause of photoallergic contact dermatitis. Indeed, many sunscreen molecules penetrate the skin causing photoallergies, phototoxic reactions and skin irritation (Marcato et al., 2011: *"Nanostructured polymer and lipid carriers for sunscreen. Biological effects and skin permeation"*, J. Nanoscience and Nanotechnology, vol. 11, 1880-1886). In addition, systemic absorption of oxybenzone following its topical application on the skin has been reported (Burnett and Wang, 2011: *"Current sunscreen controversies: a critical review"*, Photodermatology, Photoimmunology & Photomedicine, vol. 27, pages 58-67,). Aside from its photoallergic potential, major concerns regarding its systemic absorption profile has engendered heated debates regarding the overall safety of this molecule.

Avobenzone, a dibenzoylmethane derivative (butyl methoxydibenzoylmethane; trade names Parsol® 1789, Eusolex® 9020, Escalol® 517 and others) is an oil soluble ingredient used in sunscreen products to absorb the full spectrum of UV-A rays. Its ability to absorb ultraviolet light over a wider range of UVA wavelengths than many organic sunscreen agents has led to its use in many commercial preparations marketed as "broad spectrum" sunscreens. Avobenzone, as a sunscreen active, becomes photounstable and tends to degrade chemically after prolonged exposure to ultraviolet radiation (UVR). Chemical degradation of avobenzone eliminates its ability to absorb UVR and hence to protect skin against damaging UV rays when it is used as a sunscreen active in sunscreen products.

Some of the presently known sunscreen compositions contain more than one type of UV filter. Such compositions are often characterized in that the UV filters tend to interact, leading to a situation where the UV filter activity of one or more of the UV filters in the composition is reduced during storage or after being applied to the skin.

European Patent No. 1899015 discloses topical composition containing at least two different kinds of sunscreen agents, wherein at least one kind of sunscreen agent is encapsulated in microcapsules having an average, particle size of between 3 μm to 8 μm. Microcapsules smaller than 3 μm were sown to leak. The microcapsules are obtainable by an emulsion polymerization process or by a sol-gel process, wherein the encapsulating agent is a tetraalkoxysilane. Sol-gel microcapsules comprising sunscreen agents are disclosed in U.S. Pat. No. 6,303,149. These microcapsules were designed to permanently encapsulate the sunscreen agents, but a significant amount of leakage of the sunscreen agents through the microcapsules was observed when the microcapsules were incorporated into usual sunscreen compositions, particularly when the microcapsules were of size smaller than 3 μm.

Marcato et al., 2011 discloses polymeric and solid lipid nanoparticles as carriers of benzophenone-3 (BZ3), aiming to improve the safety of sunscreen products by decreasing BZ3 skin penetration and decreasing BZ3 concentration in sunscreen formulation. BZ3 is encapsulated in poly (ε-caprolactone) (PCL) nanoparticles by the nanoprecipitation method and in solid lipid nanoparticles (SLN) by the hot high pressure homogenization method. The particles were stable for 40 days. After which time the encapsulated BZ3 was released.

U.S. Pat. Nos. 6,932,984 and 7,838,037, by the present assignee, disclose a method for microencapsulation of substances by the solvent removal method using non-chlorinated solvents. The method is based on physical processes which do not cause any change of original physical and/or chemical properties, biological activity, and safety of raw materials during the process. This method affords physical stability of the microcapsules, high ability to entrap the active agents, protection of the active agents inside the microcapsules, and prevention of the diffusion of the microencapsulated active agents to the external water phase in a water-based preparation. In U.S. Pat. No. 7,838,037 the resulting microcapsules are double-layer and/or triple-layer microcapsules, designed to rupture by a slight mechanical action such as rubbing or pressing on the skin, and thereby immediately release their encapsulated content. WO 2009/138978, by the present assignee, discloses cosmetic compositions, including sunscreen compositions, comprising double-layer, rupturable microcapsules which contain one or more microencapsulated colorants, inter alia, titanium oxide. WO 2009/138978 discloses a 45 SPF sunscreen, color-changing composition comprising non-encapsulated sunscreens such as $TiO_2$ and zinc oxide.

SUMMARY OF THE INVENTION

There is an unmet need for safer sunscreen products, which are capable of increasing the sun protection factor (SPF), while eliminating cosmetic drawbacks related to the appearance of the sunscreens formulation on the skin, and, moreover, decreasing hazardous effects such as skin penetration, photodegradation, systemic absorption and toxicity of UV filters such as $TiO_2$, oxybenzone, avobenzone and other UV filters as currently used.

For example, it is highly desirable to decrease oxybenzone concentration in a sunscreen formulation, to photostabilize avobenzone and/or to overcome incompatibilities between different UV filters.

According to an aspect of some embodiments of the present invention there is provided a microcapsule comprising a core comprising at least one sunscreen agent and a shell enveloping the core, the shell being comprised of a wall-forming polymeric material comprising at least one polymer or copolymer capable of forming a plurality of hydrogen bonds and/or having an average molecular weight ranging from 5,000 Daltons to 300,000 Daltons, the microcapsule being non-breakable upon being rubbed or pressed on the skin.

According to some embodiments of the present invention, the microcapsule is non-breakable when subjected to homogenization at 2000 rpm for 10 minutes and/or to ultrasonication at 15 W and 28 kHz for 1 minute.

According to some embodiments of the present invention, the at least one polymer or copolymer have a plurality of backbone units each independently having the general structure:

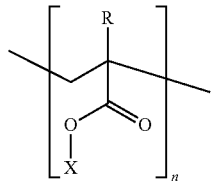

wherein:
n represents the number of backbone units in the polymer or copolymer which feature the structure;
R is alkyl; and
X is selected from the group consisting of hydrogen, alkyl, cycloalkyl, and ammonium.

According to some embodiments of the present invention, the shell is devoid of a plasticizer.

According to some embodiments of the present invention, the shell is transparent.

According to some embodiments of the present invention, the sunscreen agent is a water insoluble or water immiscible sunscreen agent, as described herein.

According to some embodiments of the present invention, the microcapsule has a size within a range selected from about 1 μm to about 100 μm, from about 1 μm to about 90 μm, from about 1 μm to about 80 μm, about 1 μm to about 70 μm, 1 μm about to about 60 μm, about 1 μm to about 50 μm, about 1 μm to about 40 μm, about 1 μm to about 30 μm, about 1 μm to about 20 μm, about 1 μm to about 10 μm, or about 2 μm to about 10 μm, or about 2 μm to about 15 μm.

According to some embodiments of the present invention, sunscreen agent is a blend of $TiO_2$ and one or more of avobenzone, p-aminobenzoic acid, cinoxate, dioxybenzone, ecamsule, homosalate, menthyl anthranilate, octocrylene, octyl salicylate, octyl-methoxycinnamate, oxybenzone, trolamine salicylate, or ZnO.

According to some of any of the embodiments of the present invention, the wall-forming polymeric material comprises a polymer or copolymer selected from the group consisting of a polyacrylate, a polymethacrylate, a cellulose ether, a cellulose ester, or any combination thereof.

According to some embodiments of the present invention, the wall-forming polymeric material comprises poly(methyl methacrylate) exhibiting MW within the range of 15,000 Daltons to 120,000 Daltons, ammonium methacrylate copolymer type B, cellulose ethyl ether, cellulose ethyl ester, or any combination thereof.

According to some of any of the embodiments of the present invention, the amount of the wall-forming polymeric material is within a range selected from about 20% to about 70%, from about 20% to about 50%, from about 20% to about 40%, or from about 20% to about 30%, or about 20% or 50%, by weight.

According to some of any of the embodiments of the present invention, the microcapsule further comprises a photostabilizer.

According to some embodiments of the present invention, the amount of the photostabilizer in the microcapsule is within a range selected from about 5% to about 50%, from about 5% to about 40%, from about 5% to about 30%, or from about 10% to about 25%, or about 10% by weight.

According to some of any of the embodiments of the present invention, the microcapsule is transparent.

According to an aspect of some embodiments of the present invention there is provided a composition comprising a plurality of microcapsules, at least a portion of the microcapsules comprising a plurality of sunscreen agent-containing microcapsules as described in any one of the respective embodiments.

According to some embodiments of the present invention, the microcapsules in the plurality of sunscreen agent-containing microcapsules are the same or different.

According to some embodiments of the present invention, the plurality of microcapsules have a mean size within a range selected from about 1 to about 100 μm, from about 1 to about 90 μm, from about 1 to about 80 μm, about 1 to about 70 μm, 1 about to about 60 μm, about 1 to about 50 μm, about 1 to about 40 μm, about 1 to about 30 μm, about 1 to about 20 μm, about 1 to about 10 μm, or about 2 to about 10 μm, or about 2 to about 15 μm.

According to some embodiments of the present invention, the composition further comprises a photostabilizer.

According to some embodiments of the present invention, at least a portion of microcapsules in the plurality of sunscreen agent-containing microcapsules further comprise a photostabilizer.

According to an aspect of some embodiments of the present invention there is provided a process of preparing sunscreen agent-containing microcapsules, the process comprising:

(a) mixing a solution comprising the sunscreen agent, a wall-forming polymeric material and an organic solvent, to thereby obtain a homogeneous solution;

(b) mixing the homogeneous solution with an aqueous solution containing an emulsifier, under high shear stirring, to thereby form an emulsion; and (c) adding to the formed emulsion an amount of water which initiates extraction of the organic solvent from the emulsion, thereby obtaining the microcapsules.

According to some embodiments of the present invention, the process further comprises isolating the microcapsules.

According to some embodiments of the present invention, the sunscreen agent-containing microcapsules are as defined in the present invention.

According to some embodiments of the present invention, the plurality of sunscreen agent-containing microcapsules in the composition as defined herein are prepared according to the process of the present invention.

According to an aspect of some embodiments of the present invention there is provided a cosmetic or cosmaceutical formulation comprising a sunscreen composition according to any one of the respective embodiments described herein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
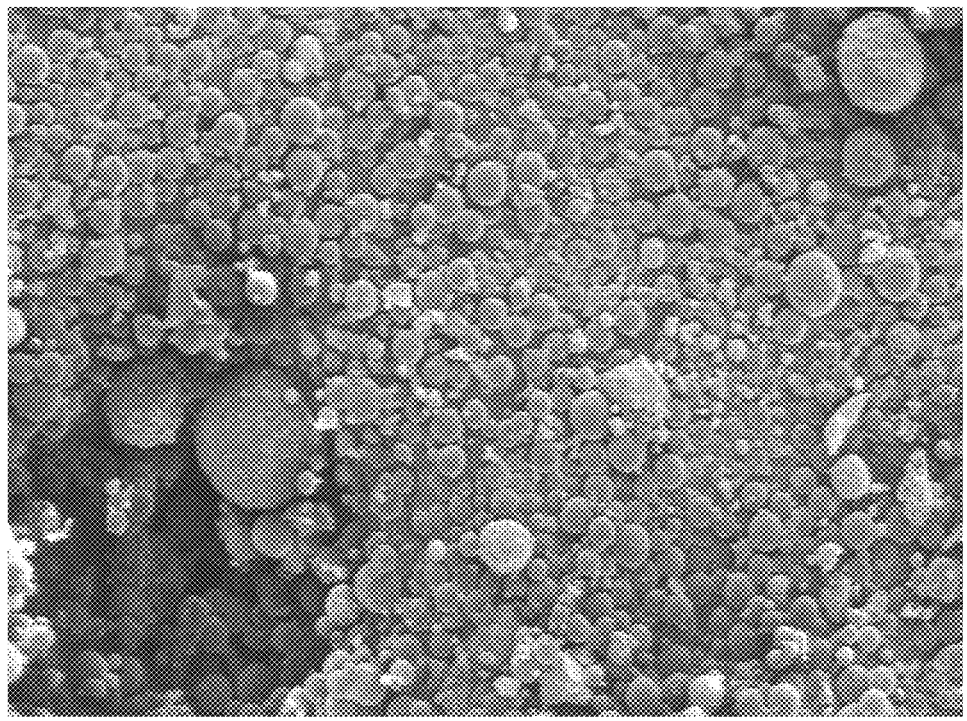
FIGS. 1A-1B present scanning electron microscope (SEM) images of microcapsules comprising poly(methyl methacrylate) (PMMA) and encapsulated $TiO_2$ in magnification ×1000 and ×5000, respectively.

The present invention, in some embodiments thereof, relates to microcapsules suitable for use in topical compositions and, more particularly, but not exclusively, to microcapsules comprising sunscreen agents and to topical formulations comprising same, which can be used, for example, in cosmetic formulations, such as sunscreen and skincare formulations.

Before explaining at least one embodiment of the invention in detail, it is to be understood that the invention is not necessarily limited in its application to the details set forth in the following description or exemplified by the Examples.

In view of the recognized need for safer sunscreen products that circumvent and even eliminate the cosmetic drawbacks and health hazards associated with known sunscreen products, and in view of the further need to provide sunscreen products exhibiting an increased sun protection factor (SPF), efforts have been made for designing sunscreen formulations that would have the benefits of an efficient UV filtering ability of UV filters such as $TiO_2$, oxybenzone, avobenzone and other UV filters as currently used, low concentrations of such sunscreen agents in formulations, chemical and photostability of the sunscreen agents during prolonged storage and, especially, during application on the skin, and, at the same time, minimum hazardous and detrimental effects to the user.

The present inventors have used the microencapsulation technique for encapsulating sunscreen agents within firm, non-rupturable microcapsules that, on one hand, protect the encapsulated sunscreen agent from destabilizing effects of light/sun, elevated temperatures and incompatible components in the formulation and, on the other hand, protect the user from harmful and endangering effects associated with direct contact of the sunscreen agent with the skin, and with systemic absorption thereof.

The present inventors have conceived utilizing the solvent removal method using non-chlorinated solvents for encapsulating sunscreen agent. The solvent removal method is based on physical processes which do not cause any change of original physical and/or chemical properties, biological activity, and safety of raw materials during the process. This method affords physical stability of the microcapsules, high ability to entrap the active agents, protection of the active agents inside the microcapsules, and prevention of the diffusion of the microencapsulated active agents to the external water phase in a water-based preparation.

Thus, the present inventors have designed and successfully practiced a novel methodology for obtaining stable and safe-to-use sunscreen formulations, which exhibit exceptional performance even at low concentrations of sunscreen agents, and which is useful, inter alia, in formulations containing sunscreen agents which are known either to have undesirable effects to the skin such as irritation, toxicity and systemic absorption, and/or as being chemically unstable.

For example, the present inventors have demonstrated that microencapsulating sunscreen agents using the methodology as described herein, enables formulating sunscreen agents such as avobenzone and $TiO_2$ at lower concentrations than commonly practiced, can photostabilize photodegradable agents such as avobenzone and/or overcomes incompatibilities between different UV filters and other components of the formulation, while maintaining and even improving the SPF of the formulation.

Microcapsules provided by the invention are available usually in powder form and consist of particles (e.g., generally spherical particles), which are generally closed structures containing an encapsulated (entrapped) substance, which comprises or consists of, in accordance with preferred embodiments, a sunscreen agent or a blend of sunscreen agents. The particle generally has the chore-shell structural feature, namely it is comprised of a polymeric shell and a core that comprises the sunscreen agent or may be consisted of the sunscreen agent, enveloped by the shell. The polymeric shell is frequently applied as a wall-forming material, and serves as a membrane for the encapsulated substance. The wall forming material of the sunscreen-containing microcapsules provided by the present invention does not contain a plasticizer, and the microcapsules are non-rupturable upon rubbing or pressing on the skin. In some embodiments, the shell of the sunscreen-containing microcapsules is transparent.

The microcapsules of the present invention, among other uses, are intended for topical, e.g., cosmetic, cosmaceutical and pharmaceutical (e.g., dermatological) applications. While applied on the skin, the microcapsules are capable of sustaining shear forces such as rubbing and pressing on the skin and remain intact so as to keep the encapsulated UV filters therewithin, segregated and separated from the other components of the formulation. The microcapsules are hard enough to avoid destruction of the shell and realization of the content during technological process by isolation, drying, sieving, etc.

The Microcapsules:

According to an aspect of some embodiments of the present invention there is provided a microcapsule which comprises a core comprising at least one sunscreen agent and a shell comprised of a wall-forming polymeric material enveloping the core. Such microcapsules are also referred to herein as sunscreen-containing microcapsule.

According to some embodiments of the invention, a microcapsule as described herein is non-rupturable or non-breakable when applied to the skin; that is, a microcapsule as described herein remains intact when applied to skin, e.g., sustains its structure and shape, when subjected to shear forces that are applied when a microcapsule is rubbed or pressed on the skin.

Non-breakability of the microcapsules of the present invention can be determined by the microcapsules' ability to remain intact, e.g., to maintain particle size and shape unchanged, following an ultrasonication for 1 minute, or homogenization at 2000 rpm for 10 minutes.

In an exemplary assay for determining non-breakability of microcapsules as described herein, microcapsules are incorporated into a base formulation such as a body lotion and subjected to ultrasonication (15 W, 28 kHz) for 1 minute.

In another exemplary assay for determining non-breakability of microcapsules as described herein, microcapsules are incorporated into a base formulation and subjected to low sheer mixing and high sheer mixing (homogenizer) at 2000 rpm for 10 minutes.

In each of these assays, the microcapsules are then observed by light microscopy, and a change in a shape or a size thereof, compared to a size and a shape of the microcapsules before subjected to an assay as described herein is determined. A change of less than 10% in the microcapsule size is indicative of the non-breakability of the microcapsules.

In some embodiments, microcapsules are subjected to one or both of the assays as described herein, and a change in the microcapsule size is observed in less than 10% of the microcapsules.

In some embodiments, the microcapsules containing the sunscreen agent as described herein are prepared by the solvent removal method, as described in further detail hereinunder.

In some embodiments, a size of the microcapsules as described herein is within a range selected from about 1 to about 100 μm, from about 1 to about 90 μm, from about 1 to about 80 μm, from about 1 to about 70 μm, from about 1 to about 60 μm, from about 1 to about 50 μm, from about 1 to about 40 μm, from about 1 to about 30 μm, from about 1 to about 20 μm, from about 1 to about 10 μm, or from about 2 to about 10 μm, preferably about 2 to about 15 μm, including any subranges and any intermediate values therebetween.

The Wall-Forming Polymer:

The phrase "wall-forming polymer", which is also referred to herein as "wall-forming polymeric material" refers to a polymeric material (e.g., a polymer or copolymer) or a combination of two or more different polymeric materials, as defined herein, which form a component of the external wall or layer or shell of the microcapsules. The term "polymer shell" refers to a polymer layer comprised of the wall-forming polymer(s).

In some embodiments, the wall-forming polymer is selected so as to sustain shear forces used when the microcapsule is applied (e.g., rubbed or pressed) on the skin.

In some embodiments, the wall-forming polymeric material comprises a polymer having a relatively low molecular weight, containing a sufficient amount of functional groups which are capable of forming hydrogen bonds.

Without being bound by any particular theory, it is assumed that polymeric material capable of forming strong hydrogen bonds is capable of forming a stabilized shell layer which accounts for the non-breakable feature of the microcapsule.

In some embodiments, the polymeric material comprises hydrogen bond-forming functional groups featuring 4-40% wt of total polymer weight.

Hydrogen bond-forming functional groups include, but are not limited to, functional groups which comprise one or more electron-donating atom(s) such as oxygen, sulfur and/or nitrogen.

Exemplary hydrogen bond-forming groups include, but are not limited to, carboxylic acid, carboxylate, carboxyalkyl, hydroxy, hydroxyalkyl, thiol, amine, amide, amidoalkyl alkoxy alkanoyloxy, alkylcarbonylalkyl, thiohydroxy and thioalkoxy, and any combination thereof.

In some embodiments, the hydrogen bond-forming groups include carboxylic acid, carboxylate, hydroxy, or any combination thereof.

In some embodiments, the wall-forming polymeric material comprises a polyacrylate, a polymethacrylate, a cellulose ether or ester, or any combination thereof.

In some of any of the embodiments of the present invention, the wall-forming polymeric material comprises a polyacrylate, or a polymethacrylate and/or comprises one or more polymers or copolymers which can be collectively represented as comprising the following general structure:

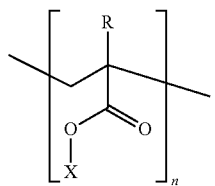

wherein:
n represents the number of backbone units in the polymer or copolymer that feature the above general structure,
R is alkyl and X is selected from the group consisting of hydrogen, alkyl, cycloalkyl, and ammonium.

When X is ammonium, a counter ion such as, for example, halide, is included.

Polymers or copolymers useful in the polymeric material of embodiments of the present invention preferably contain the backbone units described herein in an amount of about 10% to about 40% of total number of backbone units in the polymer or copolymer.

In some embodiments, the polymer is a copolymer comprising a mixture of backbone units having the above structure, whereby the units differ from one another by the type of R and/or the type of X.

In some embodiments, the polymer or copolymer comprises backbone units having the above general structure, in which R is methyl and X is methyl, thus including backbone units of PMMA.

In some embodiments, the polymeric material comprises a copolymer comprising PMMA units, and additional backbone units independently featuring the above structure.

In some embodiments, in some of the additional backbone units, X is ethyl.

In some embodiments, in some of the additional backbone units X is ammonium, for example, trimethyl ammonium chloride.

In some embodiments, the wall-forming polymeric material comprises ammonium methacrylate copolymer type B (poly(ethyl acrylate)-co-(methyl methacrylate)-co-(trimethylammonium-ethyl methacrylate chloride), also known as Eudragit RSPO® or EuRSPO®).

Any combination of polymers and co-polymers as described herein is contemplated for the wall-forming material.

In some other embodiments, the polymeric material comprises a cellulose ether or ester such as, but not limited to, methyl cellulose, ethyl cellulose, hydroxypropyl methyl cellulose, hydroxypropyl cellulose, cellulose acetate, cellulose acetate phthalate, or hydroxypropyl methyl cellulose acetate phthalate. When cellulose or derivatives thereof are used in the polymeric material, they preferably contain about 4-20% hydroxyl groups free to form hydrogen bonds.

In some of any of the other embodiments of the present invention, the wall-forming polymeric material comprises a combination of the above-mentioned polymers such as, but not limited to, combinations of Eudragit RSPO® with either PMMA or ethyl cellulose (EC).

In some of any of the embodiments of the present invention, the shell of the microcapsules comprises one or more polymers or copolymers (e.g., as described herein), having a molecular weight (MW) in the range of from 5,000 Daltons to 300,000 Daltons.

In embodiments wherein PMMA is the polymer comprised in the shell, it is preferably a polymer having a molecular weight within the range of 15,000 Daltons to 120,000 Daltons.

Without being bound by any particular theory, it is assumed that relatively low MW of the polymers or copolymers comprising the wall-forming polymeric material, and hence relatively short polymeric chains, account for non-breakability of the shell.

The amount (weight/weight) of the wall-forming polymeric material from the total microcapsule weight can be within a range selected from about 20% to about 70%, from about 20% to about 50%, from about 20% to about 40%, from about 20% to about 30%, preferably about 20% or 50%, by weight, including any subranges and any intermediate values therebetween.

The shell of the microcapsules can be transparent, semi-transparent or non-transparent and is preferably transparent. "Transparency" as used herein means more than 70% of light transmission. Thus, transparent polymers will transmit 70% to 100% of the light, while semi-transparent will transmit up to 50% of the light. In some exemplary embodiments, the microcapsules of the invention comprise a shell comprised of PMMA, as described herein, and a core containing a sunscreen agent with or without the photostabilizer, as described herein.

A further technical feature of the sunscreen-containing microcapsules of the present embodiment, which further accounts for their ability to sustain shear forces and remain non-breakable upon application, is that they comprise a wall-forming material that does not contain a plasticizer.

Thus, the sunscreen-containing microcapsules provided by some embodiments of the present invention are essentially devoid of a plasticizer.

In some embodiments, the shell of the microcapsules is devoid of a plasticizer.

As use herein in the context of the shell, "devoid of a plasticizer" means that the amount of plasticizer is less than 5%, less than 3%, less than 1% less than 0.5% less than 0.1%, less than 0.05% and even 0%, by weight, of the shell.

The Sunscreen Agent:

The terms "sunscreen agents", "sunscreens", "UV filters", "sunscreen actives" and "sun blocks" are used herein interchangeably and refer to compounds that partially block or screen UA radiation by absorbing UV radiation (such as oxybenzone) or reflecting UV rays (such as titanium dioxide, zinc oxide), or a combination thereof. The above terms are meant to encompass all groups of sunscreens, including, but not limited to, UVA sunscreens, which block UV radiation in the wavelength range of about 320 to 400 nm, UVB sunscreens, which block radiation in the range of 290 to 320 nm, and the broad spectrum agents which block all ranges.

In some of any of the embodiments described herein, the sunscreen agents are water insoluble or water immiscible sunscreen agents.

In some of any of the embodiments described herein, the sunscreen agents are water dispersible or oil soluble sunscreen agents.

Non-limiting examples of such agents include $TiO_2$, avobenzone, p-aminobenzoic acid, bemotrizinol, benzophenone-9, bexophenome-3, bisoctrizole, 3-(4-methylbenzylidene)-camphor, cinoxate, diethylamino hydroxybenzoyl hexyl benzoate, dioxybenzone, drometrizole trisiloxane, ecamsule, ethylhexyl triazone, homosalate, menthyl anthranilate, octocrylene, octyl salicylate, iscotrizinol, isopentenyl-4-methoxycinnamate, octyl-dimethyl-p-aminobenzoic acid, octyl-methoxycinnamate, oxybenzone, polysilicone-15, trolamine salicylate, ZnO, and any combination thereof.

In some of any of the embodiments of the present invention, the sunscreen agent is a UV filter approved by the US Food and Drug Administration (FDA). Non-limiting examples of FDA-approved water insoluble agents include $TiO_2$, avobenzone, p-aminobenzoic acid, cinoxate, dioxybenzone, ecamsule, homosalate, menthyl anthranilate, octocrylene, octyl salicylate, octyl-methoxycinnamate, oxybenzone, trolamine salicylate, or ZnO.

In exemplary embodiments, the UV filter is Avobenzone.

Each of the sunscreen agents described herein can be used in any combination, and with each of the embodiments described herein for the microcapsules and/or the formulation/composition containing same.

According to some embodiments, a microcapsule may be loaded with a mixture of sunscreen agents, for example, with a mixture of two or more of $TiO_2$, avobenzone, p-aminobenzoic acid, bemotrizinol, benzophenone-9, bexophenome-3, bisoctrizole, 3-(4-methylbenzylidene)-camphor, cinoxate, diethylamino hydroxybenzoyl hexyl benzoate, dioxybenzone, drometrizole trisiloxane, ecamsule, ethylhexyl triazone, homosalate, menthyl anthranilate, octocrylene, octyl salicylate, iscotrizinol, isopentenyl-4-methoxycinnamate, octyl-dimethyl-p-aminobenzoic acid, octyl-methoxycinnamate, oxybenzone, polysilicone-15, trolamine salicylate, and ZnO.

In some of any of the embodiments of the present invention, the UV filter is a mixture of FDA approved UV filters, such as $TiO_2$, avobenzone, p-aminobenzoic acid, cinoxate, dioxybenzone, ecamsule, homosalate, menthyl anthranilate, octocrylene, octyl salicylate, octyl-methoxycinnamate, oxybenzone, trolamine salicylate, or ZnO.

In some embodiments, a microcapsule is loaded with a mixture of $TiO_2$ and one or more of the FDA approved UV filters.

In some embodiments sunscreen agents which exhibit different properties, for example, UVA blocking, UVB blocking or reflection, are mixed together.

In some of any of the embodiments described herein, the amount of the sunscreen agent in a microcapsule ranges from about 20% to about 90% by weight, referring to the total weight of each microcapsule. For example, the amount can be from about 20 to about 80%, from about 40 to about 80%, preferably about 40% or 80%, by weight, including any subranges and any intermediate values therebetween.

According to some of any of the embodiments of the present invention, the sunscreen agent microencapsulated in the microcapsule is $TiO_2$. In certain features of these embodiments, the amount of $TiO_2$ in the microcapsule is within a range selected from about 25 to about 95%, from about 30 to about 90%, from about 40 to about 90%, from about 50 to about 90%, from about 60 to from about 90%, from about 70 to about 90%, from about 80 to about 90%, preferably about 80%, of the total weight of each microcapsule, including any subranges and any intermediate values therebetween.

In some of any of the embodiments of the present invention, the sunscreen agent being microencapsulated in the microcapsule is avobenzone. According to certain features of these embodiments, the amount of avobenzone in the microcapsules is within a range selected from about 30 to about 90%, from about 35 to about 90%, from about 40 to about 90%, from about 50 to about 90%, from about 60 to about 90%, from about 70 to about 90%, from about 80 to about 90%, preferably about 40%, by weight, including any subranges and any intermediate values therebetween.

Sunscreen Composition:

According to an aspect of some embodiments of the present invention there is provided a composition which comprises a plurality of microcapsules, at least a portion of the microcapsules are microcapsules which comprise a core comprising at least one sunscreen agent and a shell comprised of a wall-forming polymeric material enveloping the core, as described in any one of the embodiments described herein. Such a composition is also referred to herein as a sunscreen composition.

In some embodiments, at least 10%, at least 20%, at least 30%, at least 40%, at least 50%, at least 60%, at least 70%, at least 80%, at least 90%, at least 95%, at least 98%, or at least 99% of the plurality of microcapsules in the composition are sunscreen-containing microcapsules as described in any one of the embodiments described herein.

"Composition" as used herein refers to a plurality of microcapsules, which can be the same or can feature a plurality or variety of features. In accordance with the present invention, at least a portion of the plurality of microcapsules exhibits all the technical features characterizing a microcapsule of the invention, according to any one of the embodiments thereof, for example, having a core-shell structure, encapsulating a sunscreen agent, being non-breakable upon rubbing on the skin, being transparent and not containing a plasticizer.

The term "at least a portion" means at least 20%, at least 50%, at least 70%, at least 60%, at least 80%, at least 90%, at least 95%, at least 98%, at least 99% or all of the microcapsules being the core-shell, non-breakable sunscreen-containing microcapsules, as described in any one of the respective embodiments herein.

In some embodiments, the sunscreen-containing microcapsules as described herein in the composition can be the same, or can differ from one another by the sunscreen agent encapsulated therein and/or by the wall-forming polymeric material comprising the shell.

In the at least part or portion of the plurality of microcapsules of the composition provided by the invention, the sunscreen agent may be the same or different, and/or the microcapsules may encapsulate a mixture of sunscreens in their core.

In some embodiments related to the composition of the invention, particularly to that portion of plurality of microcapsules in the composition that exhibits the combination of technical features that characterize a microcapsule of the invention, each microcapsule can contain one of a mixture of two of more agents, preferably a mixture of at least one UVA blocker with at least one UVB blocker. In some other embodiments, microcapsules containing one agent can be mixed with microcapsules containing another agent or mixture of agents, within the sunscreen composition.

In exemplary embodiments, the combination of UVA and UVB blockers include aminobenzoic acid (a UVB filter) and avobenzone (a UVA filter), or avobenzone and $TiO_2$ (UVA and UVB filter), or octocrylene (UVB) and avobenzone, or cinoxate (UVB) and $TiO_2$, or avobenzone and octocrylene and meradimate (menthyl anthranilate) (UVA).

In some embodiments, the composition as described herein further comprises one or more additives. Exemplary additives include, but are not limited to, a photostabilizer, and a non-water soluble antioxidant.

In some embodiments, the composition further comprises a photostabilizer. The photostabilizer can be included in one or more of the microcapsules in the composition, optionally in combination with a sunscreen agent as described herein.

In some embodiments, at least a portion of the sunscreen-containing microcapsules of the invention further comprise a photostabilizer, e.g., in the core.

Photostabilizers are organic compounds that help to prevent UV filters from losing their effectiveness in sunlight. Certain photostabilizers help stabilizing UV filter molecules structurally and geometrically through electrostatic and van der Waals interactions, which makes them less likely to take part in chemical reactions. Other photostabilizers protect sunscreens by helping dissipating the energy from UV more quickly, thus reducing or even eliminating the possibility of a chemical reaction. This process is called energy transfer, and it can take place when the sunscreen agent and photostabilizer molecules exchange electrons. In this way, the sunscreen agents are fully active in protecting the skin by absorbing the harmful rays, while the photostabilizers dispose of the energy.

Non-limiting examples of photostabilizers include diethylhexyl-2,6-naphthalate (Corapan® TQ), octocrylene, or 4-methylbenzylidene camphor (MBC).

In some of any of the embodiments of the present invention, the amount of the photostabilizer in the microcapsules is within a range selected from about 5% to about 50%, from about 5% to about 40%, from about 5% to about 30%, or from about 10% to about 25%, preferably about 10%, by weight, including any subranges and any intermediate values therebetween.

Each of the microcapsules described herein can be used in any combination, and with each of the embodiments described herein for the formulation/composition containing same.

In some embodiments, a average size of the sunscreen-containing microcapsules in the sunscreen composition as described herein is within a range selected from about 1 to about 100 μm, from about 1 to about 90 μm, from about 1 to about 80 μm, from about 1 to about 70 μm, from about 1 to about 60 μm, from about 1 to about 50 μm, from about 1 to about 40 μm, from about 1 to about 30 μm, from about 1 to about 20 μm, from about 1 to about 10 μm, or from about 2 to about 10 μm, preferably about 2 to about 15 μm, including any subranges and any intermediate values therebetween.

Exemplary Sunscreen Compositions:

In some exemplary embodiments, at least a portion of a plurality of microcapsules comprising the composition of the invention comprise $TiO_2$ as the sunscreen agent in an amount of about 80% by weight, and the wall-forming material comprises poly(methyl methacrylate) in an amount of about 20% by weight.

Example 1 herein describe microcapsules containing $TiO_2$ as the sunscreen agent in an amount of about 80% by weight, and PMMA in an amount of about 20%, by weight.

Example 2 herein describes avobenzone-containing microcapsules that further contain the photostabilizer octocrylene. These microcapsules contain about 40% by weight avobenzone, about 50% by weight PMMA, and about 10% by weight octocrylene. It is demonstrated in Example 8 herein that sunscreen formulations comprising such avobenzone-octocrylene microcapsules exhibited higher photostability.

In further exemplary embodiments the sunscreen agent is homosalate and the microcapsules according to these embodiments contain about 40% by weight homosalate and about 60% by weight PMMA, or the sunscreen agent is octyl methoxycinnamate, and the microcapsules contain about 30% by weight octyl methoxycinnamate, about 70% by weight PMMA, and about 2% by weight of the stabilizer BHT (Butylated Hydroxy Toluene). In further embodiments, the sunscreen agent is octisalate, and the microcapsules contain about 40% by weight octisalate and about 60% by weight PMMA.

In further exemplary embodiments, the sunscreen agent is avobenzone in an amount of about 40% by weight, the wall-forming material is poly(methyl methacrylate) in an amount of about 50% by weight, and a photostabilizer which is octocrylene is also comprised in the composition, in an amount of about 10% by weight.

The sunscreen-containing microcapsules provided herein have several advantages. When administered to the skin in a sunscreen formulation, they retain the sunscreen on the superficial layers of the skin; maintain or improve the safety and photoprotection ability of the sunscreen agent against the detrimental effects of UV radiation; reduce systemic absorption of the sunscreen agent; and increase photostability of the sunscreen active.

In addition, the $TiO_2$-containing microcapsules reduce the agglomeration of $TiO_2$ aggregates which enables formulators to create a product that can offer high SPF efficacy, low whitening effect and better tactile properties.

The Process:

The process used for the preparation of the microcapsules of the invention as described herein is based on the microencapsulation solvent removal method disclosed, for example, in U.S. Pat. Nos. 6,932,984 and 7,838,037 and WO 2012/156965, which are incorporated by reference as if fully set forth herein. According to this technology, the active ingredient is found in the core of the microcapsule. This technique seals each micro-capped ingredient from chemical and cross-link reactions, degradation, color change or loss of potency during production, and for extended periods in storage.

For example, in certain embodiments, the microcapsules according to the present invention can be prepared by the solvent removal method comprising the following steps:
 (a) mixing a solution comprising the sunscreen agent, a wall-forming polymeric material and an organic solvent, to thereby obtain a homogeneous solution;
 (b) mixing the homogeneous solution with an aqueous solution containing an emulsifier, under high shear stirring, to thereby form an emulsion; and
 (c) adding to the formed emulsion an amount of water which initiates extraction of the organic solvent from the emulsion, thereby obtaining the microcapsules.

These steps are further detailed as follows:

The homogenous solution prepared in step (a) is obtained by preparing an organic solution of the UV filter with a wall-forming polymeric material selected from an acrylate, a polymethacrylate, a cellulose ether, a cellulose ester, or a combination thereof, in an organic solvent that is partially miscible in water and is capable of dissolving or dispersing the wall-forming polymer, optionally with one or more additives such as photostabilizing agents, and mixing/stirring until a homogeneous, optionally transparent, solution is obtained.

In step (b) the solution prepared in (a) is mixed with an aqueous solution containing an emulsifier, under high sheer stirring, to form an emulsion, which is added in step (c) to an excess amount of water to initiate extraction of the organic solvent from the emulsion, thus obtaining microcapsules.

In further steps, the emulsion is (c) left for a time sufficient to allow sedimentation of the microcapsules; and (d) the microcapsules are isolated by centrifugation/filtration, subsequently washed with water or with water optionally comprising a substance that stabilizes the microcapsules during production, such as 0.1% EDTA. Then, the wet microcapsules are dried, and sifted, resulting in a free flowing powder form.

In some embodiments, drying stage can be done using different techniques such as fluid bed, spray drying or lyophillization. In alternative embodiments, the emulsion obtained in step (b) is spray dried.

In the context of embodiments of the invention, the term "high sheer stirring" refers to a mixing at about 1000-8000 rpm, preferably at about 1000-3000 rpm, that provides smaller microcapsules. For example, an average particle size of $TiO_2$ microcapsules obtained under stirring at 2500 rpm, ranges from 2 to 15 μm, as shown in Example 1 (step 1.2), and FIGS. 1A-1B. For avobenzone microcapsules, the average particle size obtained under stirring at 2500 rpm ranges from 2 to 15 μm, as shown in Example 2 (step 2.2), and FIG. 2.

Topical Formulations:

In certain embodiments, the composition provided herein is used in cosmetic, cosmaceutical or pharmaceutical formulations such as sunscreens and skincare formulations or dermatological or other topical pharmaceutical formulations, comprising the microcapsules as described herein (e.g., a sunscreen composition as described herein). The formulation can optionally and preferably further comprise a carrier, and optionally additional active agents and/or additives.

As used herein a "formulation" refers to a preparation comprising sunscreen compositions as described herein, with other chemical components such as cosmetic, cosmaceutic or pharmaceutical agents (e.g., drugs), physiologically acceptable carriers and excipients.

As used herein, the term "physiologically acceptable" means approved by a regulatory agency of the Federal or a state government or listed in the U.S. Pharmacopeia or other generally recognized pharmacopeia for use in animals, and more particularly in humans.

Herein, the phrase "physiologically suitable carrier" refers to an approved carrier or a diluent that does not cause significant irritation to an organism and does not abrogate the biological activity and properties of the administered conjugate.

Herein the term "excipient" refers to an inert substance added to a pharmaceutical composition to further facilitate processes and administration of the active ingredients.

Sunscreens are important skin-care products used for preventing photoaging and skin cancer. Sunscreen compositions that contain mixtures of UVA and UVB type sunscreen actives may provide an SPF (sun protection factor) of from 2 to 50.

In some embodiment of the present invention, the cosmetic or cosmaceutical formulation is formulated in a form suitable for topical application on the applied area.

By selecting the appropriate carrier and optionally other ingredients that can be included in the composition, as is detailed hereinbelow, the compositions of the present invention may be formulated into any form typically employed for topical application.

The formulations can be water based, oil based or silicon based.

In some embodiments, a formulation as described is in a form of a cream, an ointment, a paste, a gel, a lotion, a milk, an oil, a suspension, a solution, an aerosol, a spray, a foam, or a mousse.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emolliency). As with other carriers or vehicles, an ointment base should be inert, stable, nonirritating and nonsensitizing. As explained in *Remington: The Science and Practice of Pharmacy,* 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the sunscreens-containing microcapsules, are present in a water or alcohol base. Lotions are typically preferred for covering/protecting large body areas, due to the case of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethyl-cellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base. Depending on the nature of the base, pastes are divided between fatty pastes or those made from a single-phase aqueous gels. The base in a fatty paste is generally petrolatum, hydrophilic petrolatum and the like. The pastes made from single-phase aqueous gels generally incorporate carboxymethylcellulose or the like as a base. Additional reference may be made to *Remington: The Science and Practice of Pharmacy*, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or hydroalcoholic, but are typically formulated with high alcohol content which, upon application to the skin of a user, quickly evaporates, driving the active ingredient through the upper skin layers to the site of treatment.

In some embodiments, the composition comprising a plurality of microcapsules, at least a portion thereof encapsulate sunscreens, is a lotion as demonstrated in Example 3 or base cream as demonstrated in Example 4.

The preparation of the formulation can be carried out by mixing and homogenizing all the ingredients except for the sunscreens microcapsules, and adding the sunscreens microcapsules at the end, followed by homogenization of the mixture (as exemplified in Example 4). Alternatively, in some cases, the preparation of the formulation can be carried out by mixing sunscreens microcapsules with the other ingredients of the formulation and homogenizing the mixture, wherein the other ingredients of the formulation may optionally be heated to obtain a homogeneous solution, and cooled prior to the addition of the UV filter microcapsules (as exemplified in Example 3).

The microcapsules of the invention can be used in pharmaceutical compositions for topical application, which include, for example, pharmaceutically active agents for dermatological or transdermal applications.

In any of the formulations described herein, additional agents and/or additives can be included. These agents and/or additives and can be encapsulated or non-encapsulated.

In some embodiments, one or more of these agents and/or additives is encapsulated.

In some of these embodiments, the agents and/or additives are encapsulated using microcapsules as described in any one of U.S. Pat. Nos. 6,932,984 and 7,838,037, and WO 2009/138978.

Some non-limiting representative examples of additives and/or agents include humectants, deodorants, antiperspirants, sunless tanning agents, hair conditioning agents, pH adjusting agents, chelating agents, preservatives, emulsifiers, occlusive agents, emollients, thickeners, solubilizing agents, penetration enhancers, anti-irritants, colorants, propellants and surfactants.

Representative examples of humectants include, without limitation, guanidine, glycolic acid and glycolate salts (e.g. ammonium slat and quaternary alkyl ammonium salt), aloe vera in any of its variety of forms (e.g., aloe vera gel), allantoin, urazole, polyhydroxy alcohols such as sorbitol, glycerol, hexanetriol, propyleneglycol, butylene glycol, hexylene glycol and the like, polyethylene glycols, sugars and starches, sugar and starch derivatives (e.g., alkoxylated glucose), hyaluronic acid, lactamide monoethanolamine, acetamide monoethanolamine and any combination thereof.

Suitable pH adjusting agents include, for example, one or more of adipic acids, glycines, citric acids, calcium hydroxides, magnesium aluminometasilicates, buffers or any combinations thereof.

Representative examples of deodorant agents include, without limitation, quaternary ammonium compounds such as cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmlthyl sarcosine, lauroyl sarcosine, N-myristoyl glycine, potassium N-lauryl sarcosine, stearyl, trimethyl ammonium chloride, sodium aluminum chlorohydroxy lactate, tricetylmethyl ammonium chloride, 2,4,4'-trichloro-2'-hydroxy diphenyl ether, diaminoalkyl amides such as L-lysine hexadecyl amide, heavy metal salts of citrate, salicylate, and piroctose, especially zinc salts, and acids thereof, heavy metal salts of pyrithione, especially zinc pyrithione and zinc phenolsulfate. Other deodorant agents include, without limitation, odor absorbing materials such as carbonate and bicarbonate salts, e.g. as the alkali metal carbonates and bicarbonates, ammonium and tetraalkylammonium carbonates and bicarbonates, especially the sodium and potassium salts, or any combination of the above.

Antiperspirant agents can be incorporated in the compositions of the present invention either in a solubilized or a particulate form and include, for example, aluminum or zirconium astringent salts or complexes.

Representative examples of sunless tanning agents include, without limitation, dihydroxyacetone, glyceraldehyde, indoles and their derivatives. The sunless tanning agents can be used in combination with the sunscreen agents.

The chelating agents are optionally added to formulations so as to enhance the preservative or preservative system. Preferred chelating agents are mild agents, such as, for example, ethylenediaminetetraacetic acid (EDTA), EDTA derivatives, or any combination thereof.

Suitable preservatives include, without limitation, one or more alkanols, disodium EDTA (ethylenediamine tetraacetate), EDTA salts, EDTA fatty acid conjugates, isothiazolinone, parabens such as methylparaben and propylparaben, propyleneglycols, sorbates, urea derivatives such as diazolindinyl urea, or any combinations thereof.

Suitable emulsifiers include, for example, one or more sorbitans, alkoxylated fatty alcohols, alkylpolyglycosides, soaps, alkyl sulfates, monoalkyl and dialkyl phosphates, alkyl sulphonates, acyl isothionates, or any combinations thereof.

Suitable occlusive agents include, for example, petrolatum, mineral oil, beeswax, silicone oil, lanolin and oil-soluble lanolin derivatives, saturated and unsaturated fatty alcohols such as behenyl alcohol, hydrocarbons such as squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Suitable emollients include, for example, dodecane, squalane, cholesterol, isohexadecane, isononyl isononanoate, PPG Ethers, petrolatum, lanolin, safflower oil, castor oil, coconut oil, cottonseed oil, palm kernel oil, palm oil, peanut oil, soybean oil, polyol carboxylic acid esters, derivatives thereof and mixtures thereof.

Suitable thickeners include, for example, non-ionic water-soluble polymers such as hydroxyethylcellulose (commercially available under the Trademark Natrosol® 250 or 350), cationic water-soluble polymers such as Polyquat 37 (commercially available under the Trademark Synthalen® CN), fatty alcohols, fatty acids and their alkali salts and mixtures thereof.

Representative examples of solubilizing agents that are usable in this context of the present invention include, without limitation, complex-forming solubilizers such as citric acid, ethylenediamine-tetraacetate, sodium meta-phosphate, succinic acid, urea, cyclodextrin, polyvinylpyrrolidone, diethylammonium-ortho-benzoate, and micelle-forming solubilizers such as TWEENS and spans, e.g., TWEEN 80. Other solubilizers that are usable for the compositions of the present invention are, for example, polyoxyethylene sorbitan fatty acid ester, polyoxyethylene n-alkyl ethers, n-alkyl amine n-oxides, poloxamers, organic solvents, phospholipids and cyclodextrines.

Suitable penetration enhancers include, but are not limited to, dimethylsulfoxide (DMSO), dimethyl formamide (DMF), allantoin, urazole, N,N-dimethylacetamide (DMA), decylmethylsulfoxide ($C_{10}$ MSO), polyethylene glycol monolaurate (PEGML), propyleneglycol (PG), propyleneglycol monolaurate (PGML), glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. The permeation enhancer may also be a vegetable oil. Such oils include, for example, safflower oil, cottonseed oil and corn oil.

Suitable anti-irritants include, for example, steroidal and non steroidal anti-inflammatory agents or other materials such as aloe vera, chamomile, alpha-bisabolol, cola nitida extract, green tea extract, tea tree oil, licoric extract, allantoin, caffeine or other xanthines, glycyrrhizic acid and its derivatives.

Exemplary additional active agents according to this embodiment of present invention include, without limitation, one or more, or any combination of an antibiotic agent, an antimicrobial agent, an anti-acne agent, an anti-aging agent, a wrinkle-reducing agent, a skin whitening agent, a sebum reducing agent, an antibacterial agent, an antifungal agent, an antiviral agent, a steroidal anti-inflammatory agent, a non-steroidal anti-inflammatory agent, an anesthetic agent, an antipruriginous agent, an antiprotozoal agent, an anti-oxidant, an antineoplastic agent, an immunomodulator, an interferon, an antidepressant, an anti histamine, a vitamin, a hormone and an anti-dandruff agent.

Examples of these include alpha-hydroxy acids and esters, beta-hydroxy acids and ester, polyhydroxy acids and esters, kojic acid and esters, ferulic acid and ferulate derivatives, vanillic acid and esters, dioic acids (such as sebacid and azoleic acids) and esters, retinol, retinal, retinyl esters, hydroquinone, t-butyl hydroquinone, mulberry extract, licorice extract, and resorcinol derivatives.

Suitable anti-acne agents for use in this context of the present invention include, without limitation, keratolytics such as salicylic acid, sulfur, glycolic, pyruvic acid, resorcinol, and N-acetylcysteine and retinoids such as retinoic acid and its derivatives (e.g., cis and trans, esters).

Suitable antibiotics for use in this context of the present invention include, without limitation, benzoyl peroxide, octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate and cholate.

Representative examples of non-steroidal anti-inflammatory agents that are usable in this context of the present invention include, without limitation, oxicams, such as piroxicam, isoxicam, tenoxicam, sudoxicam, and CP-14, 304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamate, a flufenamic acid derivative, is particularly useful for topical application.

Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, fluc-etonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluorometholone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Suitable antipruritic agents include, without limitation, pharmaceutically acceptable salts of methdilazine and trimeprazine.

Non-limiting examples of anesthetic drugs that are suitable for use in context of the present invention include pharmaceutically acceptable salts of lidocaine, bupivacaine, chlorprocaine, dibucaine, etidocaine, mepivacaine, tetracaine, dyclonine, hexylcaine, procaine, cocaine, ketamine, pramoxine and phenol.

Suitable antimicrobial agents, including antibacterial, antifungal, antiprotozoal and antiviral agents, for use in context of the present invention include, without limitation, beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, farnesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octoprirox, parachlorometa xylenol, nystatin, tolnaftate and clotrimazole and mixtures thereof.

Non-limiting examples of anti-oxidants that are usable in the context of the present invention include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the trade name Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

Non-limiting examples of antineoplastic agents usable in context of the present invention include daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A and XR9576.

Non-limiting examples of antidepressants usable in context of the present invention include norepinephrine-reuptake inhibitors ("NRIs"), selective-serotonin-reuptake inhibitors (SSRIs), monoamine-oxidase inhibitors (MAOIs), serotonin-and-noradrenaline-reuptake inhibitors ("SNFIs), corticotropin-releasing factor (CRF) antagonists, α-adreno-receptor antagonists, NK1-receptor antagonists, 5-HT$_{1A}$-receptor agonist, antagonists, and partial agonists and atypical antidepressants, as well as norepinephrine-reuptake inhibitors such as, but are not limited to amitriptyline, desmethylamitriptyline, clomipramine, doxepin, imipramine, imipramine-oxide, trimipramine; adinazolam, amiltriptylinoxide, amoxapine, desipramine, maprotiline, nortriptyline, protriptyline, amineptine, butriptyline, demexiptiline, dibenzepin, dimetacrine, dothiepin, fluacizine, iprindole, lofepramine, melitracen, metapramine, norclolipramine, noxiptilin, opipramol, perlapine, pizotyline, propizepine, quinupramine, reboxetine, tianeptine, and serotonin-reuptake inhibitors such as, but are not limited to, binedaline, m-chloropiperzine, citalopram, duloxetine, etoperidone, femoxetine, fluoxetine, fluvoxamine, indalpine, indeloxazine, milnacipran, nefazodone, oxaflazone, paroxetine, prolintane, ritanserin, sertraline, tandospirone, venlafaxine and zimeldine.

Exemplary anti-dandruff agents include, without limitation, zinc pyrithione, shale oil and derivatives thereof such as sulfonated shale oil, selenium sulfide, sulfur; salicylic acid, coal tar, povidone-iodine, imidazoles such as ketoconazole, dichlorophenyl imidazolodioxalan, clotrimazole, itraconazole, miconazole, climbazole, tioconazole, sulconazole, butoconazole, fluconazole, miconazolenitrite and any possible stereo isomers and derivatives thereof such as anthralin, piroctone olamine (Octopirox), selenium sulfide, and ciclopirox olamine, and mixtures thereof.

Non-limiting examples of vitamins include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin B3 (niacinamide and its derivatives), alpha hydroxy acids (such as glycolic acid, lactic acid, tartaric acid, malic acid, citric acid, etc.) and beta hydroxy acids (such as salicylic acid and the like).

Non-limiting examples of dermatological active ingredients usable in context of the present invention include jojoba oil and aromatic oils such as methyl salicylate, wintergreen, peppermint oil, bay oil, eucalyptus oil and citrus oils, as well as ammonium phenolsulfonate, bismuth subgallate, zinc phenolsulfonate and zinc salicylate. Non-limiting examples of antifungal agents include miconazole, clotrimazole, butoconazole, fenticonasole, tioconazole, terconazole, sulconazole, fluconazole, haloprogin, ketonazole, ketoconazole, oxinazole, econazole, itraconazole, terbinafine, nystatin and griseofulvin.

Non-limiting examples of antihistamines usable in context of the present invention include chlorpheniramine, brompheniramine, dexchlorpheniramine, tripolidine, clemastine, diphenhydramine, promethazine, piperazines, piperidines, astemizole, loratadine and terfenadine.

It is expected that during the life of a patent maturing from this application many relevant sunscreen agents and wall-forming materials will be developed and the scope of the term "sunscreen agent" and "wall-forming polymer" is intended to include all such new technologies a priori.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "10 μm" is intended to mean "about 10 μm".

As used herein, numerical ranges preceded by the term "about" should not be considered to be limited to the recited range. Rather, numerical ranges preceded by the term "about" should be understood to include a range accepted by those skilled in the art for any given element in microcapsules or formulations according to the present invention.

The term "about" as used herein means within an acceptable error range for a particular value as determined by one of ordinary skill in the art, which will depend in part on how the value is measured or determined, i.e., the limitations of the measurement system. For example, "about" can mean a range of up to 10%, more preferably up to 5%, and still more preferably up to 1% of a given value. Where particular values are described in the application and claims, unless otherwise stated, the meaning of the term "about" is within an acceptable error range for the particular value.

The terms "comprises", "comprising", "includes", "including", "having" and their conjugates mean "including but not limited to".

The term "consisting of" means "including and limited to".

The term "consisting essentially of" means that the composition, method or microcapsules may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 5 carbon atoms. The alkyl group may be substituted or unsubstituted. When substituted, the substituent group can be, for example, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, sulfonamide, phosphonyl, phosphinyl, carbonyl, thiocarbonyl, carboxy, thiocarboxy, carbamate, thiocarbamate, amido, sulfonamido, and amino, as these terms are defined herein.

As used herein, the term "hydroxyalkyl" refers to an alkyl, as this term is defined herein, substituted by a hydroxy group, as defined herein, and includes, for example, hydroxymethyl, hydroxyethyl, hydroxypropyl and hydroxy-n-butyl.

As used herein, the term "halogen", which is also referred to herein interchangeably as "a halogen atom" or "halo", includes chloro (Cl), bromo (Br), iodo (I) and fluoro (F).

The term "alkanoyloxy" refers to a carbonyl group, as define herein and includes, for example, acetyl, propionyl, butanoyl and the like.

The term "carboxyalkyl" refers to an alkyl, as this term is defined herein, substituted by a carboxy group, as defined herein, and includes, for example, carboxymethyl, carboxyethyl, ethylenecarboxy and the like.

The term "alkylcarbonylalkyl" refers to an alkyl, as this term is defined herein, substituted by a carbonyl group, as defined herein, and includes, for example, methanoylmethyl, ethanoylethyl and the like.

The term "amidoalkyl" refers to an alkyl, as this term is defined herein, substituted by an amide group, as defined herein, and includes, for example, —$CH_2CONH_2$; —$CH_2CH_2CONH_2$; —$CH_2CH_2CH_2CONH_2$ and the like.

A "hydroxy" group refers to an —OH group.

An "alkoxy" group refers to both an —O-alkyl and an —O-cycloalkyl group, as defined herein.

A "thiohydroxy" group refers to a —SH group.

A "thioalkoxy" group refers to both an —S-alkyl group, and an —S-cycloalkyl group, as defined herein.

A "carbonyl" group refers to a —C(=O)—R' group, where R' is hydrogen, alkyl, alkenyl, cycloalkyl, aryl, heteroaryl (bonded through a ring carbon) or heteroalicyclic (bonded through a ring carbon) as defined herein.

A "thiocarbonyl" group refers to a —C(=S)—R' group, where R' is as defined herein for R'.

A "carboxy" group refers to a —C(=O)—O—R' where R' is as defined herein.

An "amino" group refers to an —NR'R" group where R' and R" are as defined herein.

An "amido" group refers to a —C(=O)—NR'R" group or a R'C(=O)—NR" group, where R' and R" are as defined herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Preparation of Microcapsules Containing $TiO_2$ 1.1 Preparation of Organic Phase/Master Batch (MB) Stage An organic phase (herein referred to interchangeably as "master batch" (MB)) was prepared by gradually adding 20 grams of the wall-forming polymer poly(methyl methacrylate) (PMMA) under stirring (5 minutes), into 233.3 grams of ethyl acetate, heating to 50° C. and stirring well until the mixture was homogeneous and transparent (about 20 minutes). The obtained polymer solution was cooled to 25° C. $TiO_2$ was added to the solution under stirring for about 5 minutes and then the mixture was homogenized for about 8 minutes. The components of the MB are presented in Table 1.

TABLE 1

| | Master batch constituents | |
|---|---|---|
| | Material | Loading for 100 grams MB |
| 1 | PMMA (average MW ca. 15,000; Sigma-Aldrich ®, IL) | 20 |
| 2 | $TiO_2$ (UV-TITAN M262, Sachtleben, Germany) | 80 |
| 3 | Ethyl acetate (Sciencelab[[.]](dot)com, Inc., USA) | 233.3 |

1.2 Preparation of the Emulsion

An aqueous solution of 0.4% polyvinyl alcohol (PVA) was prepared by mixing water (810 grams) with PVA 4% solution (90 grams). Ethyl acetate (100 grams) was added to the water phase, and then the master batch of step 1.1 above (333.3 grams) was gradually added into the ethyl acetate/water emulsion under high sheer stirring at about 2500 RPM for 2 minutes. The ratio between the master batch and the emulsion (w/w) was 1:3. The components of the emulsion are presented in Table 2.

TABLE 2

| | Emulsion constituents | |
|---|---|---|
| | Material | Loading (grams) |
| 1 | Water | 810 |
| 2 | PVA (Mowiol 4-88, KSE solution 4 %; Kuraray America, Inc., USA) | 90 |
| 3 | Ethyl Acetate (Sciencelab[[.]](dot)com, Inc., USA) | 100 |
| 4 | MB | 333.3 |

1.3 Extraction of the Organic Solvent

The extraction fluid was composed of a mixture of 6,745 grams water and 355 grams of PVA solution 4% (final concentration of PVA in the extraction fluid 0.20% PVA). The emulsion of step 1.2 above (1333.3 grams) was gradually added into the extraction fluid in a 10 L pail under stirring at 150 RPM using a manual pump, and was further stirred for additional 15 minutes. The resulting mixture was left to sediment for about 24 hours at 25° C., thus obtaining microcapsules comprising about 80% by weight of $TiO_2$ and about 20% by weight of PMMA. The components of the extraction medium are presented in Table 3.

TABLE 3

| | Extraction medium constituents | |
|---|---|---|
| | Material | Loading (grams) |
| 1 | Emulsion | 1333.3 |
| 2 | Water | 6745 |
| 3 | 4% PVA solution | 355 |

1.4 Washing, Drying and Sifting of the Microcapsules

The $TiO_2$ microcapsules obtained in step 1.3 above were separated either by centrifugation or vacuum filtration. In the centrifugation procedure, the upper liquid phase from the pail was decanted and the remaining suspension was shaken and divided into 50 ml tubes, and then centrifuged at 2000 RPM for 2 minutes. The upper liquid phase in each tube was removed, the sediment was suspended in 5 ml water, and the suspension was transferred to a drying vessel and stored at −20° C. for sample freezing. In the filtration procedure, the upper phase liquid was decanted from the pail, the remaining suspension was shaken and then filtered, and the sediment was rinsed on the filter with 400 ml water. The suspension was transferred to a drying vessel and the microcapsules were stored at −20° C. for sample freezing. In the drying stage, the microcapsules were freeze dried (lyophilized) for 48 hours.

In the sifting stage, the dried microcapsules were sifted using automatic sifter "Ari j-Levy", Sifter MIC. 100. The sifted microcapsules were stored in an appropriate container in a refrigerator.

Figure 1B:
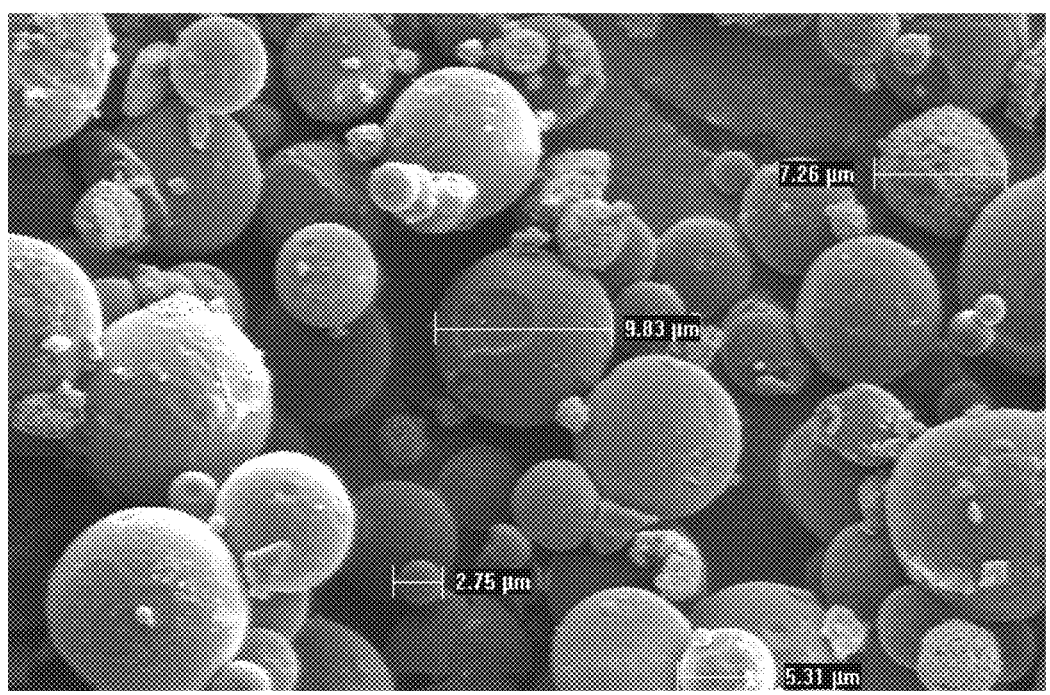

Scanning electron microscopy (SEM) images of the $TiO_2$ microcapsules prepared as described above were taken using Zeiss Ultra Gemini® (Zeiss, Germany). The SEM images of the microcapsules are presented in FIGS. 1A-1B and show that the microcapsules have a round shape form. The size of $TiO_2$ microcapsules ranges from 2.5 to 10 μm (FIG. 1B).

Example 2

Preparation of Microcapsules Containing Avobenzone 2.1 Preparation of Master Batch (MB)

A master batch was prepared under light protection conditions by gradually adding 50 grams of the wall-forming polymer PMMA, under stirring (5 minutes), into 300 grams of ethyl acetate in a vessel, heating to 50° C. and dissolving PMMA under stirring (about 20 minutes) to a homogeneous and transparent solution. The polymer solution was than cooled to 25° C., and octocrylene (10 grams) was added to the polymer solution under stirring for about 3 minutes. 1-(4-methoxyphenyl)-3-(4-tert-butylphenyl) propane-1,3-dione (avobenzone; 40 grams) was then added to the mixture under stirring for 5 minutes. The components of the MB are presented in Table 4.

TABLE 4

MB constituents

| | Material | Loading component of MB (grams)-(for 100 grams) |
|---|---|---|
| 1 | PMMA | 50 |
| 2 | Octocrylene (UNIPROMA, China) | 10 |
| 3 | Avobenzone (Neo Heliopan ® 357, 95% < OPCs, Symrise, Germany) | 40 |
| 4 | Ethyl Acetate | 300 |

2.2 Preparation of the Emulsion

An aqueous solution was prepared by mixing water (1,012.5 grams) with EDTA 0.1% (1.08 gram) and PVA (4%, 67.5 grams) such that the water phase consisted of 0.25% PVA. Ethyl acetate (120 grams) was added to the water phase, and then the master batch of step 2.1 above (400 grams) was gradually added into the ethyl acetate/water emulsion under high sheer stirring at 2500 RPM for about 2 minutes. The components of the emulsion are presented in Table 5.

TABLE 5

Emulsion constituents

| | Material | Loading for 100 g portion (grams) |
|---|---|---|
| 1 | Water | 1012.5 |
| 2 | PVA (Mowiol 4-88, KSE solution 4%) | 67.5 |
| 3 | Ethyl Acetate (10% from the total emulsion weight) | 120 |
| 4 | MB of step 2.1 | 400 |

The extraction, washing, drying, and sifting procedures are identical to the extraction, washing, drying and sifting procedures described above in steps 1.3 and 1.4 of Example 1. The extraction solution content is as detailed in Table 6 below, and the water used for suspending the sediment or rinsing the sediment on filter additionally comprised 0.1% EDTA. The microcapsules, comprised of PMMA (about 50% by weight) and containing about 40% by weight and about 10% by weight octocrylene, were obtained as a white to light yellow powder.

TABLE 6

Extraction medium constituents

| | Material | Loading (grams) |
|---|---|---|
| 1 | Emulsion | 1600 |
| 2 | Water | 8550 |
| 3 | EDTA 0.1% | 9.0 |

TABLE 6-continued

Extraction medium constituents

| | Material | Loading (grams) |
|---|---|---|
| 4 | PVA solution 4% (0.20% PVA from water phase) | 450 |

Figure 2:
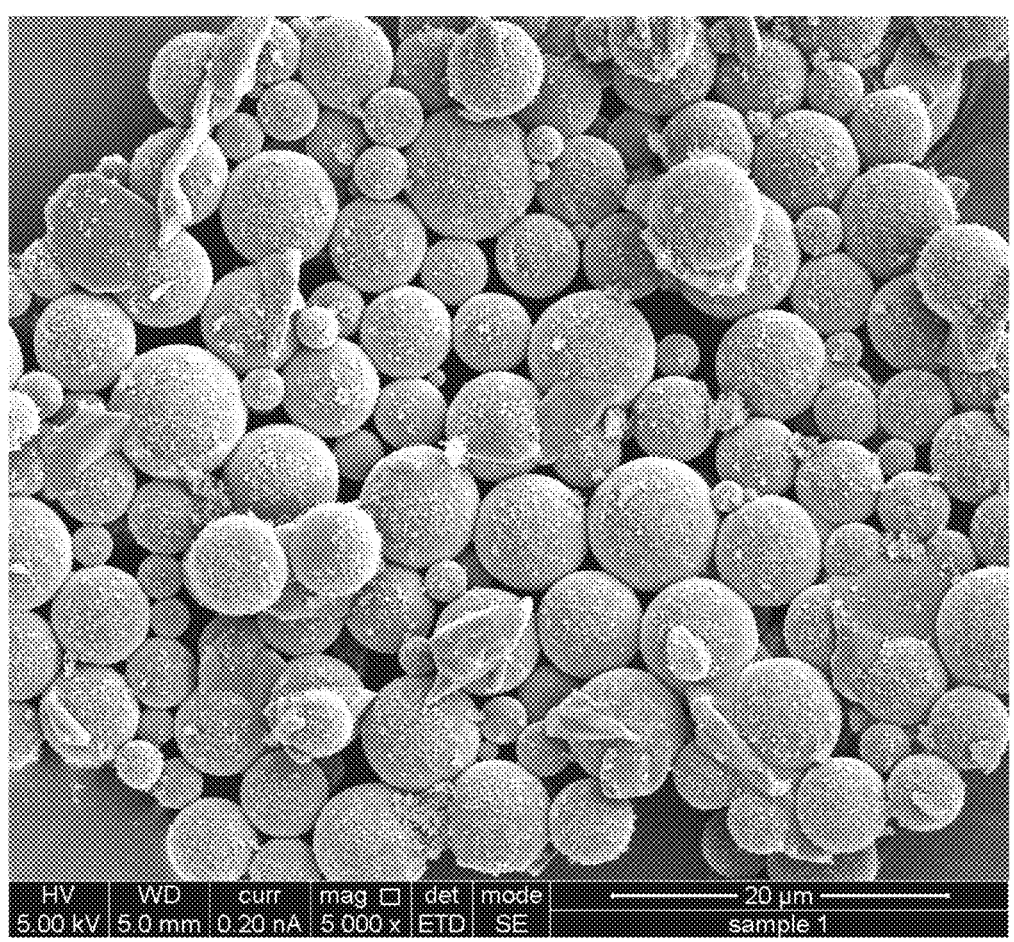
FIG. 2 presents SEM image of avobenzone-containing microcapsules comprising PMMA as the wall-forming polymer, magnified ×5000.

Scanning electron microscopy (SEM) images of the avobenzone microcapsules prepared as described above were taken using Zeiss Ultra Gemini® (Zeiss, Germany). The SEM image is depicted in FIG. 2 and shows that the microcapsules have a round shape form and their size ranges from 2.5 to 10 μm.

Example 3

Preparation of Body Lotion Sunscreen Formulation

Body lotion sunscreen formulations comprising sunscreens-containing microcapsules of some embodiments of the present invention and the ingredients listed in Table 7 below were prepared by combining 4 phases prepared separately, as follows: Phase 1 was obtained by mixing altogether the ingredients listed in Table 7 and heating to 70° C.

Phase 2, the stabilizing gel was prepared by mixing glycerin into water, followed by slow addition of the gelling-emulsifying agent Ecogel™ in order to increase viscosity and avoid clumping. The mixture was heated to 70° C. under mixing, and further mixed whilst maintaining this temperature for additional 20 minutes.

Phase 3, the sunscreen agent dispersion, was prepared by adding sunscreen agent-containing microcapsules according to some embodiments of the present invention, for example, microcapsules containing $TiO_2$, to the dispersing agent Crodasperse™ (particularly useful for inorganic pigments such as titanium oxide) using an efficient paddle type mixer at a suitable speed (depending on the mixer used) to disperse completely and evenly the UV filter microcapsules. The dispersion was then put aside.

Phase 4, the cosmetics additive solution, was prepared by adding the multifunctional cosmetics additive Geogard™ Ultra to water (to 100 mL) in a suitable vessel, and heating the mixture to 70° C. Cosmetic and toiletries additives such as Geogard™ Ultra are naturally-derived products with broad spectrum protection that improve skin moisture content, and have an exceptional toxicity profile.

The final product, sunscreen formulation, was prepared by adding to Phase 4 (aqueous solution of the cosmetics additive), the Phase 1 mixture under high speed mixing at 70° C. The stabilizing gel prepared in Phase 2 was then added and the resulting mixture was mixed and homogenized for several minutes until uniformity was obtained. The pH was measured and adjusted, when necessary, to pH 5-6 with lactic acid. The mixture was left to cool. Sepiplus™ 400, a multifunctional polymer serving as a thickening agent, was added to the mixture under strong mixing. The mixture was homogenized and cooled to 30° C. The UV filter dispersion of Phase 3 was remixed again and added to the main vessel containing the combined Phases 1+2+4 under paddle mixing until the UV filter-containing microcapsules were evenly mixed into the product. The final product was homogenized for 2-3 minutes, and cooled to room temperature.

TABLE 7

Ingredients of body lotion formulation

| Ingredient | % (weight) |
|---|---|
| Phase 1 | |
| Polyaldo ™ 10-2-P (decyl glyceril dipalmitate; emulsifier, Lonza, USA) | 5.0 |
| Dermofeel ® Sensolv (isoamyl laurate; emollient, Dr. Straetmans, Germany) | 2.0 |
| Dermofeel ® MCT (tricaprylin, emollient, Dr. Straetmans, Germany) | 2.0 |
| Refined sweet almond oil (*Prunus amygdalus* Dulcis (sweet almond) oil; emollient, Alban Muller, France) | 1.0 |
| Cetiol ® OE (dicaprylyl ether; emollient, Cognis, Germany) | 2.3 |
| Gransil PM-56 (phenyltrimethicone; skin conditioning agent, Grant, USA) | 0.5 |
| Phase 2 | |
| Ecogel ™ (Lysolecithin & Sclerotium Gum & Xanthan Gum & Pullulan, Lucas Meyer, France) | 0.54 |
| Water | 17.0 |
| Glycerin (moisturizer and humectant, Gadot, Israel) | 2.1 |
| Phase 3 | |
| UV filter microcapsules according to the invention | |
| Crodasperse ™ (caprylic/capric triglyceride & di-PPG-3 myristyl ether adipate & sorbitan stearate; dispersing agent, Croda, UK) | 18 |
| Geogard ™ Ultra (gluconolactone & sodium benzoate; preservative, Lonza, USA) | 1 |
| Lactic acid (acidity adjuster, Purac, USA) | |
| Phase 4 | |
| Sepiplus ™ 400 (polyacrylate-13 & polyisobutene & polysorbate 20; thickening agent, Seppic, France) | 1.0 |
| Water (solvent) | to 100.0 |

Example 4

Preparation of a UV Base Cream

For the preparation of a UV base cream containing sunscreen agent-containing microcapsules of some embodiments of the present invention, a base cream formulation was first prepared from the ingredients listed in Table 8. Three phases prepared separately were combined to give the final product as follows:

Phase 1, was obtained by mixing together all the ingredients listed in Table 8, and heating to 70° C. Phase 2 was prepared by mixing water and glycerin, heating to 70° C. under mixing, and then adding Phase 2 to Phase 1. Phase 3, comprising the preservative Euxyl PE 9010, was added to the combined phases 1+2 followed by mixing and homogenizing for several minutes till uniformity was obtained. The resulting mixture was cooled to 30° C. under gentle mixing, homogenized for 2 to 3 minutes, and cooled to room temperature.

TABLE 8

Ingredients for a base cream

| Ingredient | % (weight) |
|---|---|
| Phase 1 | |
| Polyaldo ™ 10-2-P (emulsifier) | 8.5 |
| Dermofeel ® Sensolv (emollient) | 3.4 |
| Dermofeel ® MCT (emollient) | 3.4 |
| Refined sweet almond oil (emollient) | 1.65 |
| Cetio ® OE (emollient) | 3.95 |
| Gransil PM-56 (skin conditioning agent) | 0.84 |
| Sepiplus ™ 400 (thickening agent) | 1.1 |
| Phase 2 | |
| Water (solvent) | 69.41 |
| Glycerin (moisturizer and humectant) | 6.75 |
| Phase 3 | |
| Euxyl ® PE 9010 (phenoxyethanol & ethylhexylglycerin preservative; Schulke, Germany) | 1.0 |

UV base cream formulations were prepared by adding the UV filter-containing microcapsules of some embodiments of the present invention, for example, microcapsules containing $TiO_2$, to the base cream formulation above, followed by homogenization.

Example 5

In Vitro SPF Measurements of a Sunscreen Formulation Comprising Microencapsulated $TiO_2$ The sun protection factor (SPF) of a sunscreen (UV base cream) formulation comprising 18.5% microencapsulated $TiO_2$ (final concentration of $TiO_2$ 15%) was measured using SPF-290S Analyzer, the WinSPF software (Optometrics, UK) and the US FDA standard protocol. In general, a 1 ml syringe was used to dispense 100 or more dabs of a sample over a Transpore® tape substrate area (70.7×70.7 mm) at the rate of 2 μl/cm², as specified by the US FDA. Results were determined by averaging results of 9 scans of sample in different locations on the Transpore® tape substrate. Each scan covered a transmittance measurement along a wave length increment of 1 nm starting from 290 up to 400 nm.

Figure 3:
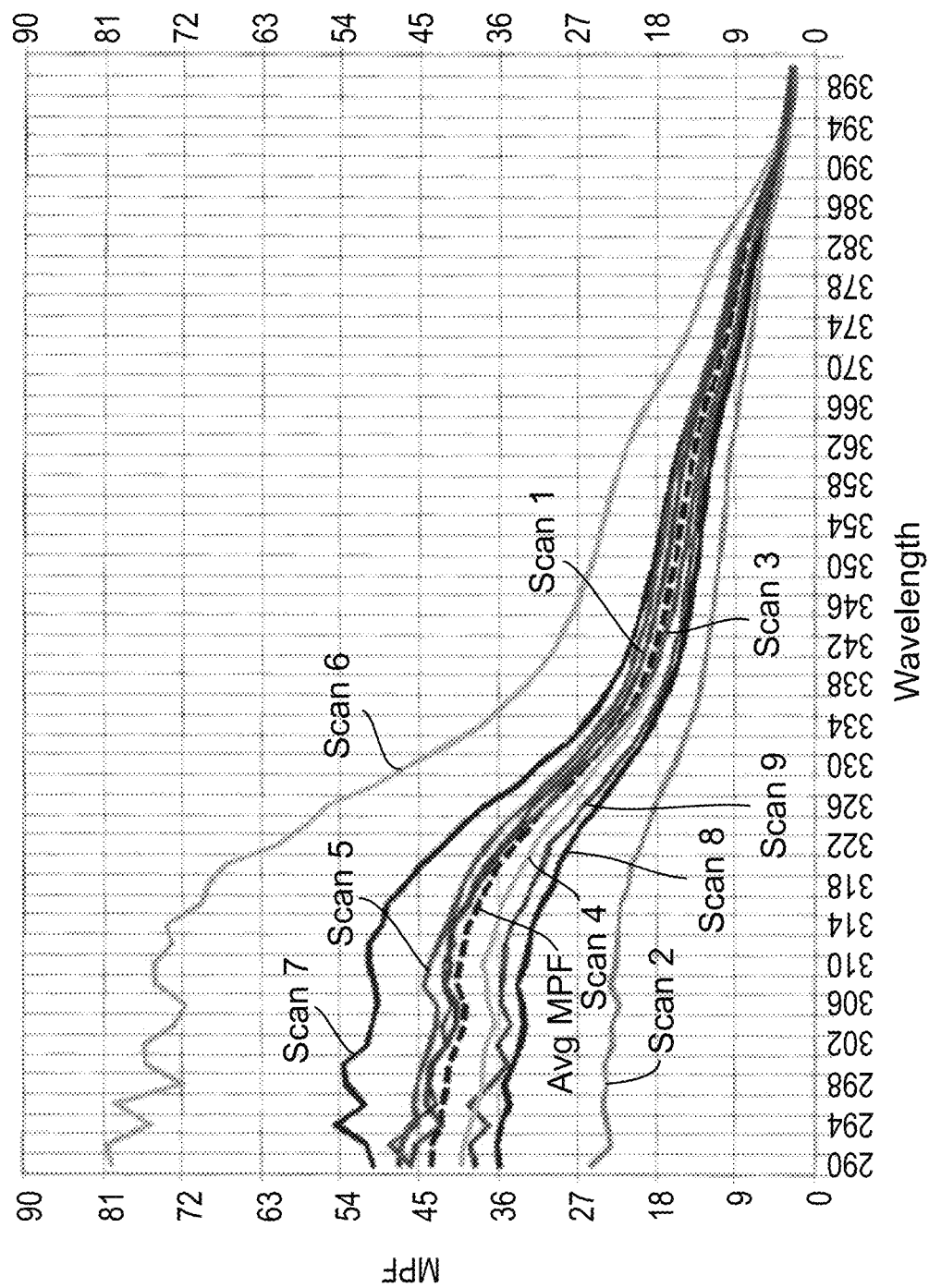
FIG. 3 is a graph presenting the monochromatic protection factor (MPF) of a sunscreen formulation comprising 15% microencapsulated $TiO_2$ as a function of the wavelength, for 9 scans taken from 9 different locations of a Transpore® tape substrate area covered with the formulation.

These measurements were compared to a reference scan at the same wavelength to compute the sample transmittance. The SPF-290S' WinSPF software converted measurements of the monochromatic protection factor (MPF) to the SPF values using established well-known calculation methods. FIG. 3 shows curves of MPF values as a function of the wavelength of a sunscreen formulation of the invention comprising 18.75% of microencapsulated $TiO_2$. The calculated SPF value was 32.19, while the UVA/UVB ratio was 0.67. These values clearly indicate that the $TiO_2$ microcapsules can serve as a UVB filter, adsorbing UV light at 280-320 nm.

Example 6

Figure 4:
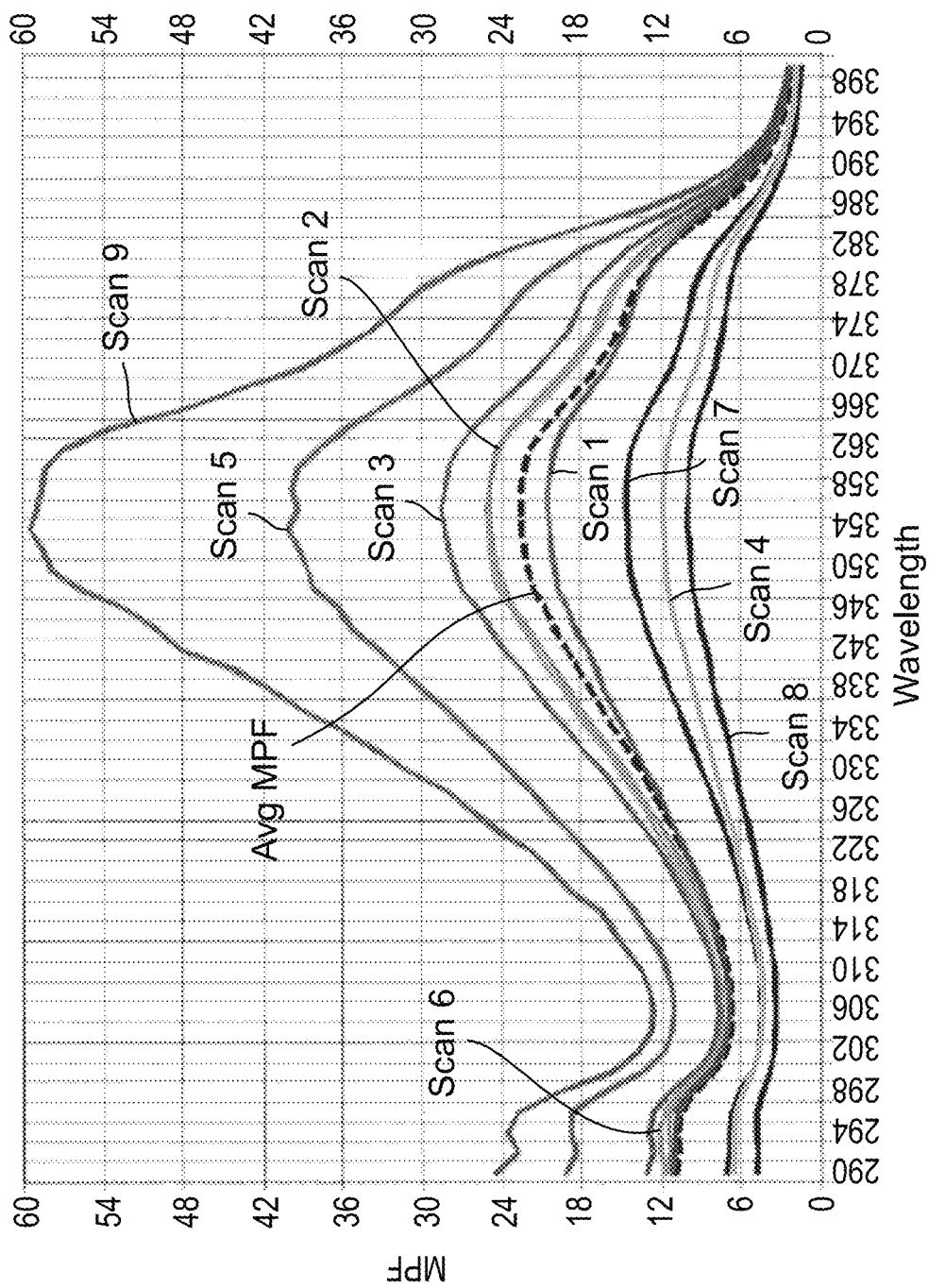
FIG. 4 is a graph presenting the monochromatic protection factor of a sunscreen formulation comprising 7.5% microencapsulated avobenzone as a function of the wavelength, for 9 scans taken from 9 different locations of a Transpore® tape substrate area covered with the formulation.

In Vitro SPF Measurements of a Sunscreen Formulation Comprising Microencapsulated Avobenzone The SPF of sunscreen (UV base cream) formulation comprising 7.5% microencapsulated avobenzone (final concentration of avobenzone was 3%) was measured using SPF-290S Analyzer, the WinSPF software (Optometrics, UK) and the FDA standard protocol, as described in Example 5. FIG. 4 shows MPF of the sunscreen formulation as a function of the wavelength for 9 scans taken from 9 different locations of a Transpore® tape substrate area covered with the formulation. The SPF value was 7.84, while the UVA/UVB ratio was 1.202. These values clearly indicate that the avobenzone microcapsules can serve as a UVA filter, adsorbing UV light at 320-400 nm.

waiting time of 15 minutes was realized. Irradiation was carried out by 6 different doses. The resultant erythema was used to ascertain the minimal erythema dose (MED). The minimal erythema dose is defined as the lowest UV dose that produces the first perceptible unambiguous erythema with defined borders appearing over most of the field of UV exposure. The MED was assessed visually 20+4 hours after exposure with controlled uniform illumination in a blind manner.

The individual sun protection factor (SPF) was determined from the ratio of MEDu (MED of untreated skin) and MEDp (MED of protected skin) of the area treated with the Test Product. An SPF result was expressed as the arithmetical mean of the individual SPF values obtained from the total number of subjects used.

Subjects that took part in this test were selected on the basis of Fitzpatrick's skin type table or on the basis of skin colour typing by colorimetric measurements, respectively (ITA°>28'). They corresponded to the majority of users as far as their skin sensitivity classification was concerned. Subjects with phototype skin termed Type I had a very light skin, and Type II skin color subjects had a light skin color.

The Test Product formulation of these embodiments of the invention and Standard P2, were applied in mean amounts of 73.2 (±1.0) mg and 72.7 (±1.2) mg, respectively, on a skin area of 36.0 $cm^2$ (amounts of application 2.03 (±0.027) and 2.02 (±0.034) $mg/cm^2$ for Test Product and P2, respectively). Irradiation was carried out by 6 different doses. The results are presented in Table 9.

TABLE 9

| In Vivo SPF measurements for a formulation containing microencapsulated avobenzone | | | | | | | | | |
|---|---|---|---|---|---|---|---|---|---|
| Characterization of subjects | | | | | | Test Product | | Standard P2 | |
| No | Age | Sex | Skin Type | ITA° | MEDu (mJ/$cm^2$) | MEDp (mJ/$cm^2$) | SPF | MEDp (mJ/$cm^{2)}$ | SPF |
| 1 | 47 | f | II | 54 | 14.9 | 92.9 | 6.3 | 302.8 | 20.4 |
| 2 | 69 | f | II | 51 | 15.9 | 99.7 | 6.3 | 406.1 | 25.5 |
| 3 | 39 | f | I | 59 | 15.2 | 90.9 | 6.0 | 308.8 | 20.4 |
| 4 | 21 | m | II | 48 | 17.6 | 105.7 | 6.0 | 448.6 | 25.5 |
| 5 | 19 | f | II | 44 | 25.0 | 120.1 | 4.8 | 326.3 | 13.0 |
| 6 | 59 | m | II | 45 | 19.8 | 148.6 | 7.5 | 403.8 | 20.4 |
| Number | | | | | 6 | 6 | 6 | 6 | 6 |
| Mean | | | | | 18.1 | 109.6 | 6.1 | 366.1 | 20.9 |
| Standard Deviation | | | | | 3.9 | 21.8 | 0.9 | 61.2 | 4.6 |
| Confidence Interval | | | | | | | 0.9 | | 4.8 |
| Confidence Interval [%] | | | | | | | 14.7 | | 23.1 |
| Lower Limit of CI | | | | | | | 5.2 | | 16.0 |
| Upper limit of CI | | | | | | | 7.1 | | 25.7 |
| Standard Error (SEM) [%] | | | | | | | 5.7 | | 8.9 |

Example 7

In Vivo SPF Measurements of a Sunscreen Formulation Comprising Microencapsulated Avobenzone The SPF of a sunscreen (UV base cream) formulation comprising 7.5% microencapsulated avobenzone (final concentration of avobenzone 3%) was measured and analyzed according to FDA final rules 2011. In the in vivo test, the sunscreen formulation of the invention (Test Product) was applied to 6 subjects, and the degree of protection provided, the SPF, was measured and compared to that obtained for a standard formulation (Standard P2, a reference formulation used as a methodological control to verify the test procedure). The mean SPF of the standard is 16.3 with 3.43 standard deviation.

Test areas on subjects' backs were coated with the test product. Between product application and irradiation, a The results presented in Table 9, show that the SPF obtained for in vivo application of the formulation containing final concentration of 3% avobenzone (7.5% of encapsulated avobenzone) was 5-7 and in line with the in vitro results obtained for this formulation (SPF 7.84). Moreover, the in vivo SPF was higher than expected for tests conducted in vivo and clearly indicates that the formulation was absorbed in the skin and provided excellent protection against UV radiation and at the maximum avobenzone concentration allowed by the FDA.

Example 8

Photostability of Nonencapsulated Versus Microencapsulated Avobenzone after Exposure to Sun Avobenzone is known to be unstable upon exposure to sunlight and tends to break down into unknown chemicals.

In the present example, the photostability of avobenzone in a body lotion sunscreen formulations comprising either non encapsulated avobenzone or microencapsulated avobenzone of the present invention was measured.

Photostability was assessed by spreading a known amount of body lotion sunscreen formulation (40±3 mg), containing either free avobenzone (non-encapsulated, raw material) or microcapsules containing about 40% by weight avobenzone and 10% by weight of the photostabilizer octocrylene obtained in Example 2 above, at a final concentration in the formulation of 3%, onto glass microscope slides at an application density of about 2 mg/cm$^2$. After application, the glass slides were left for 4 hours at maximum sun exposure in the open air. Exposure period was set from 10:00 AM to 14:00 AM at Tel-Hai, Upper Galilee, Israel, in two different dates. Non-exposed slides served as controls and were stored in the dark until extraction.

Following sun exposure, both treated and untreated glass slides were placed in 50 ml polypropylene (PP) sterile tubes. Dichloromethane (DCM, 25 ml) was added to each tube, and the tubes were roughly shaken for two minutes for complete extraction of the sunscreens. Following extraction, the samples were further diluted with DCM at 1:10 ratio, and 3 ml from the final dilution were filtered with 0.45 micron Teflon filters. UV absorbance of the DCM extracts was recorded from 280 to 400 nm using a spectrophotometer (Jasco V-53 UV/VIS Spectrophotometer). The loss in avobenzone was measured using UV spectrophotometer at 358 nm. Corrected absorbance at 358 nm due only to avobenzone was then used to obtain a calculated weight of avobenzone in the lotion from a standard curve prepared for each product.

Figure 5A:
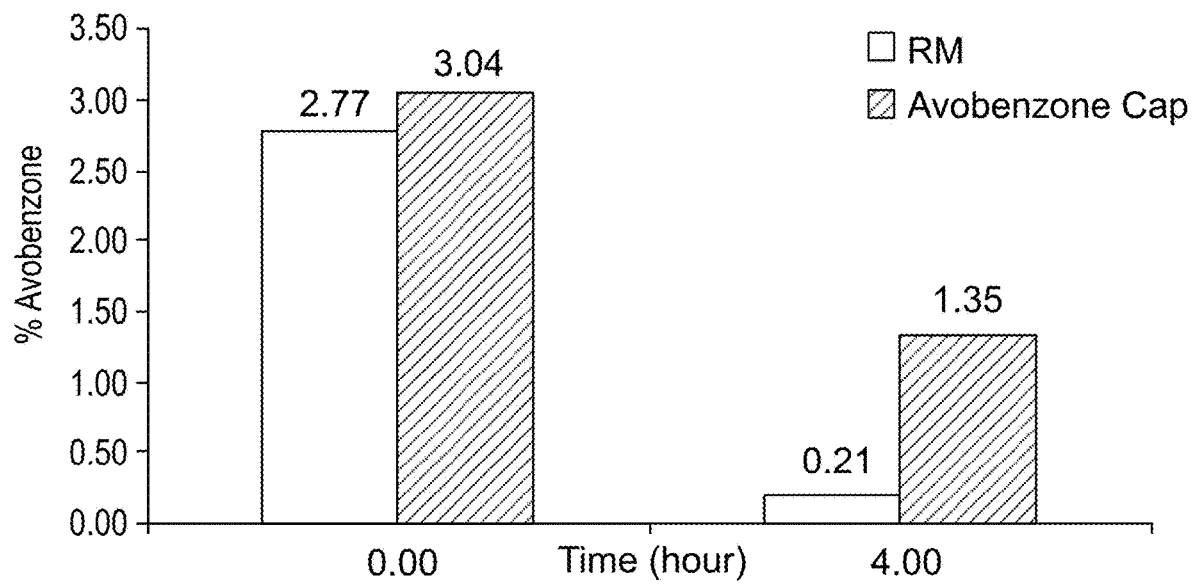
FIGS. 5A-5B are bar graphs presenting photostability test results of a sunscreen formulation containing non-encapsulated (raw) avobenzone and of a body lotion sunscreen formulation containing microcapsules comprising 40% avobenzone and 10% octocrylene. Final concentration of avobenzone in both formulation is about 3%. The bars in FIGS. 5A and 5B present % of avobenzone in each formulation before and after 4-hour exposure to sun in two different dates.
Figure 5B:
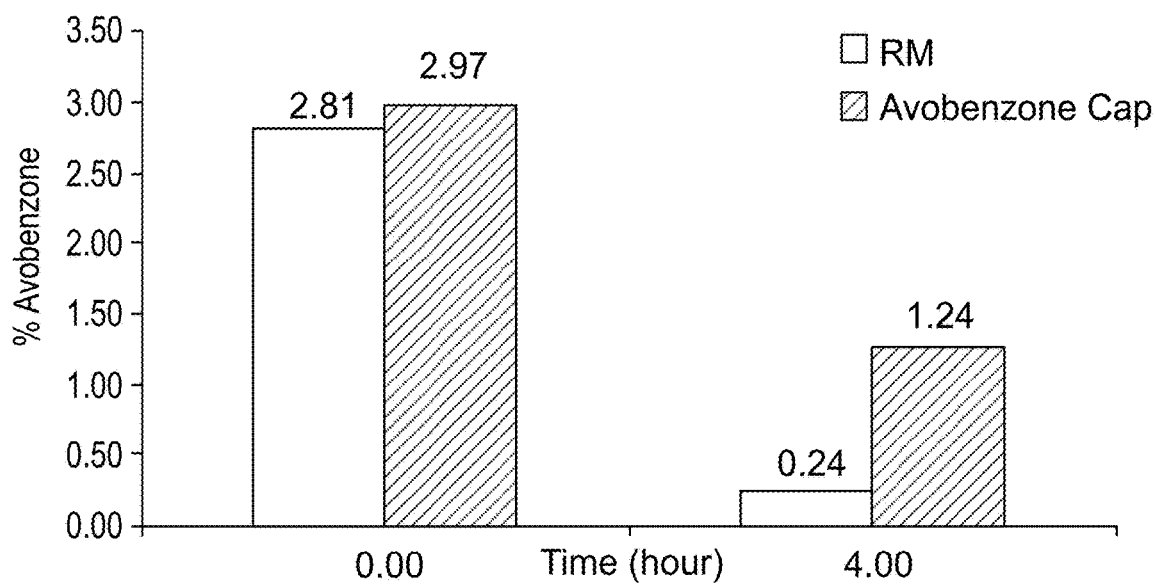

FIGS. 5A and 5B show the photostability test results for raw avobenzone (left bars) versus the microencapsulated avobenzone (right bars) in a body lotion sunscreen formulation of some embodiments of the present invention. As seen in the figures, there is a significant loss of the UV filter in the sunscreen formulation comprising raw avobenzone (reduction of UV filter concentration to 0.21% and to 0.24% in two measurements), while the sunscreen formulation with the microencapsulated avobenzone was more stable (reduction of UV filter concentration only to 1.35% and to 1.24% in two measurements). The lower concentration reduction of avobenzone was not only due to mere encapsulation thereof but further due to co-encapsulation of octocrylene. However, the octocrylene percentage was significantly lower when comparing to formulations containing non-encapsulated form of avobenzone. Usually the octocrylene level is no less than half of the avobenzone.

Example 9

Determining Breakability of Sunscreen-Containing Microcapsules

In order to assess durability of sunscreen agent containing microcapsule to shear forces, a sample of a base cream, such as the body lotion prepared in Example 3 herein, was subjected to low shear mixing by a simple paddle mixer at 50-200 rpm and/or to high shear mixing using homogenizer at 1000-2000 rpm, both for 10 minutes.

Another sample of the base cream was subjected to ultrasonication (15 W, 28 kHz) for 1 minute.

Prior to homogenization and ultrasonication, a sample of the base cream was observed under microscope and the particle sizes distribution was assessed (qualitatively). Samples of the homogenized and ultrasonicated cream containing the microcapsules of the invention were viewed under the microscope and the particle size distribution was qualitatively assessed again. A reduction in particle size of less than 10% compared to a sample that was not sonicated or homogenized indicated that the microcapsules sustained the shear force exerted upon them and classified them as non-breakable microcapsules.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A microcapsule comprising a non-aqueous core and a shell enveloping said core,
    wherein said core consists of at least one sunscreen agent that absorbs UV radiation, and said shell is composed of a wall-forming polymeric material comprising at least one polymer or copolymer selected from the group consisting of a polyacrylate, a polymethacrylate, a cellulose ether, and a cellulose ester, and said sell is devoid of a plasticizer,
    wherein the microcapsule has a mean size within a range of from 1 µm to 30 µm, and the microcapsule is non-breakable when rubbed or pressed on a skin and when subjected to an ultrasonication for 1 minute, or to homogenization at 2000 rpm for 10 minutes,
    wherein said at least one sunscreen agent is a water insoluble sunscreen agent selected from the group consisting of bemotrizinol, iscotrizinol, ethylhexyl triazone, and diethylamino hydroxybenzoyl hexyl benzoate, and
    wherein an amount of said at least one sunscreen agent in the microcapsule is within a range of from 40% to 80%; and an amount of said wall-forming polymeric material is within a range of from 20% to 50%.

2. The microcapsule of claim 1, wherein said at least one sunscreen agent is diethylamino hydroxybenzoyl hexyl benzoate.

3. The microcapsule of claim 1, wherein said at least one sunscreen agent is selected from the group consisting of bemotrizinol, iscotrizinol, and ethylhexyl triazone.

4. The microcapsule of claim 1, wherein said mean size is within a range of from 2 µm to 15 µm.

5. The microcapsule of claim 1, wherein said at least one polymer or copolymer is selected from the group consisting of a cellulose ether and a cellulose ester.

6. The microcapsule of claim 1, wherein said shell is transparent.

7. A composition comprising a plurality of microcapsules according to claim 1.

8. A cosmetic or cosmeceutical formulation comprising a plurality of sunscreen agent-containing microcapsules according to claim 1, and a cosmetically or cosmeceutically acceptable carrier.

9. A process of preparing microcapsules according to claim 1, the process comprising:
   (a) mixing a solution consisting of said at least one sunscreen agent, said wall-forming polymeric material and an organic solvent, to thereby obtain a homogeneous solution;
   (b) mixing said homogeneous solution with an aqueous solution containing an emulsifier, under high shear stirring, to thereby form an emulsion; and
   (c) adding to said emulsion an amount of water which initiates extraction of the organic solvent from said emulsion, thereby obtaining the microcapsules.

10. The microcapsule of claim 3, wherein said at least one sunscreen agent is bemotrizinol.

11. The microcapsule of claim 3, wherein said at least one sunscreen agent is iscotrizinol.

12. The microcapsule of claim 3, wherein said at least one sunscreen agent is ethylhexyl triazone.

\* \* \* \* \*